(12) United States Patent
Sakaguchi et al.

(10) Patent No.: US 8,759,323 B2
(45) Date of Patent: Jun. 24, 2014

(54) PROTEIN PHOSPHATASE INHIBITOR

(75) Inventors: Kazuyasu Sakaguchi, Sapporo (JP); Keiji Tanino, Sapporo (JP); Yoshiro Chuman, Sapporo (JP); Fumihiko Yoshimura, Sapporo (JP); Hiroaki Yagi, Sapporo (JP)

(73) Assignee: LSIP, LLC, Tokyo (JP)

( * ) Notice: Subject to any disclaimer, the term of this patent is extended or adjusted under 35 U.S.C. 154(b) by 423 days.

(21) Appl. No.: 13/123,166

(22) PCT Filed: Oct. 2, 2009

(86) PCT No.: PCT/JP2009/005128
§ 371 (c)(1),
(2), (4) Date: Jun. 10, 2011

(87) PCT Pub. No.: WO2010/041401
PCT Pub. Date: Apr. 15, 2010

(65) Prior Publication Data
US 2011/0288050 A1    Nov. 24, 2011

(30) Foreign Application Priority Data
Oct. 9, 2008  (JP) ................................ 2008-262646

(51) Int. Cl.
*A01N 55/00*  (2006.01)
*A61K 31/695*  (2006.01)
*C07F 7/04*  (2006.01)
*C07F 7/08*  (2006.01)

(52) U.S. Cl.
USPC .............................. 514/63; 556/431; 556/465

(58) Field of Classification Search
USPC ..................... 514/63; 546/431, 465
See application file for complete search history.

(56) References Cited

U.S. PATENT DOCUMENTS

2006/0036094 A1    2/2006  Miyashita

FOREIGN PATENT DOCUMENTS

JP    2006316001    11/2006

OTHER PUBLICATIONS

Total Synthesis of Norzoanthamine, Science, Jul. 23, 2004, vol. 305, pp. 495-499.
Journal of the Chemical Society, 2001, Perkins Transactions 1, pp. 2250-2256.
Chemical Communications, 2000, pp. 1463-1464.
Organic Biomolecular Chemistry, 2003, vol. 24, pp. 4364-4366.
Chemistry, A European Journal, Jul. 2009, vol. 15, pp. 6626-6644.
Nature Genetics, vol. 31, Jun. 2002, pp. 210-215.
Molecular and Cellular Biology, vol. 22, No. 4, Feb. 2002, pp. 1094-1105.
European Search Report from EPO for corresponding application in Europe, 6 pages, 2012.
Yagi, H., et al., 2009, Identification of Novel Chemical Inhibitors for p53-Inducible Protein Phosphatase PPM1D, Peptide Sci., vol. 45, pp. 385-386. [Reference D1].
PCT International Preliminary Report, PCT Written Opinion, 10 pages, 2009.

*Primary Examiner* — Samira Jean-Louis
(74) *Attorney, Agent, or Firm* — Hogan Lovells US LLP

(57) ABSTRACT

Provided is a novel protein phosphatase inhibitor. The protein phosphatase inhibitor contains, as an active ingredient, a silicon compound represented by the following general formula (1) or a salt thereof, wherein $R^1$, $R^2$ and $R^3$ are the same or different and represent a hydrocarbon group having 1 to 12 carbon atoms; X represents an optionally substituted hydrocarbon group having 3 to 36 carbon atoms or an optionally substituted heterocyclic group; and n represents an integer of 0 or 1.

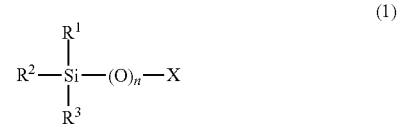

(1)

7 Claims, 5 Drawing Sheets

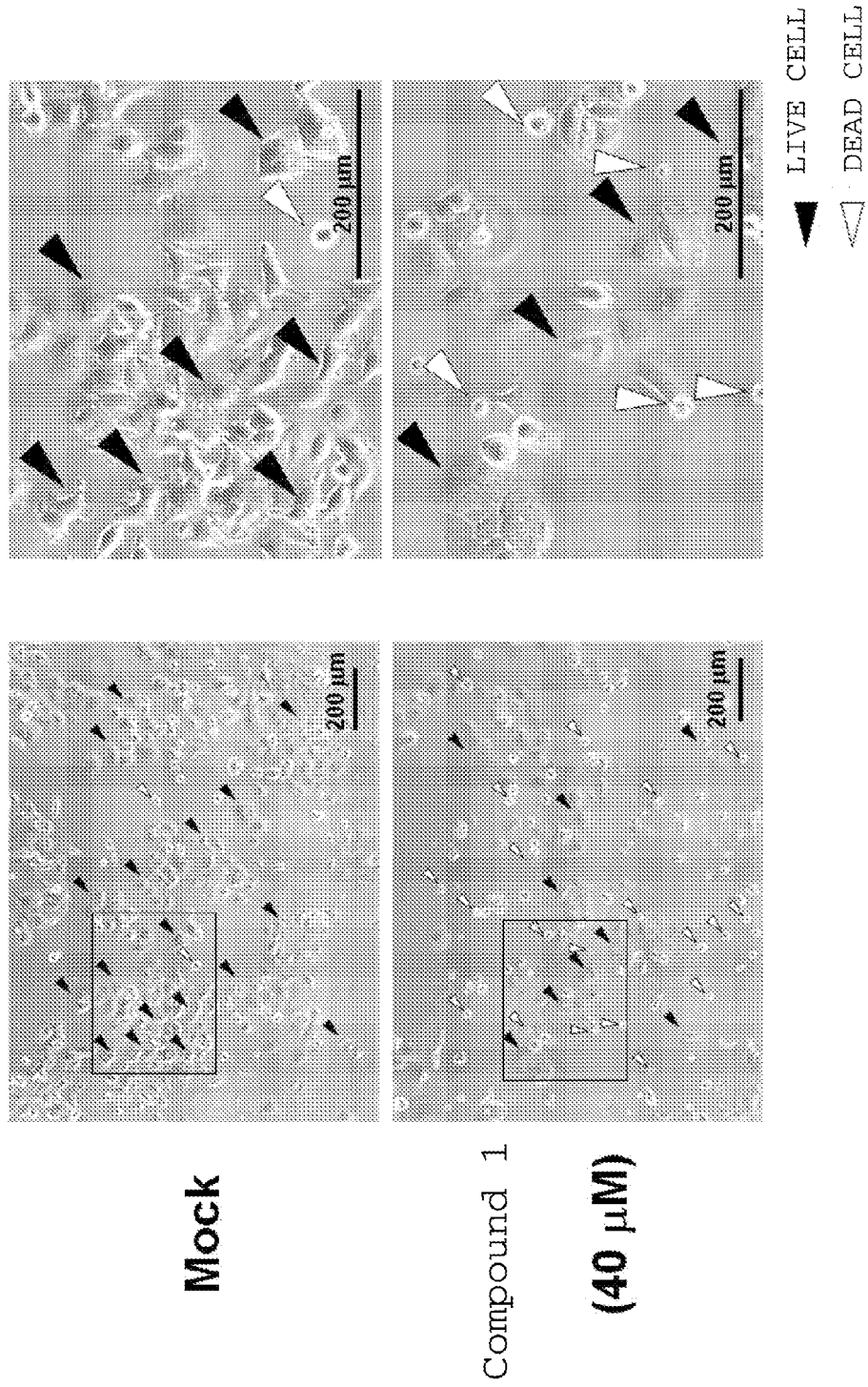

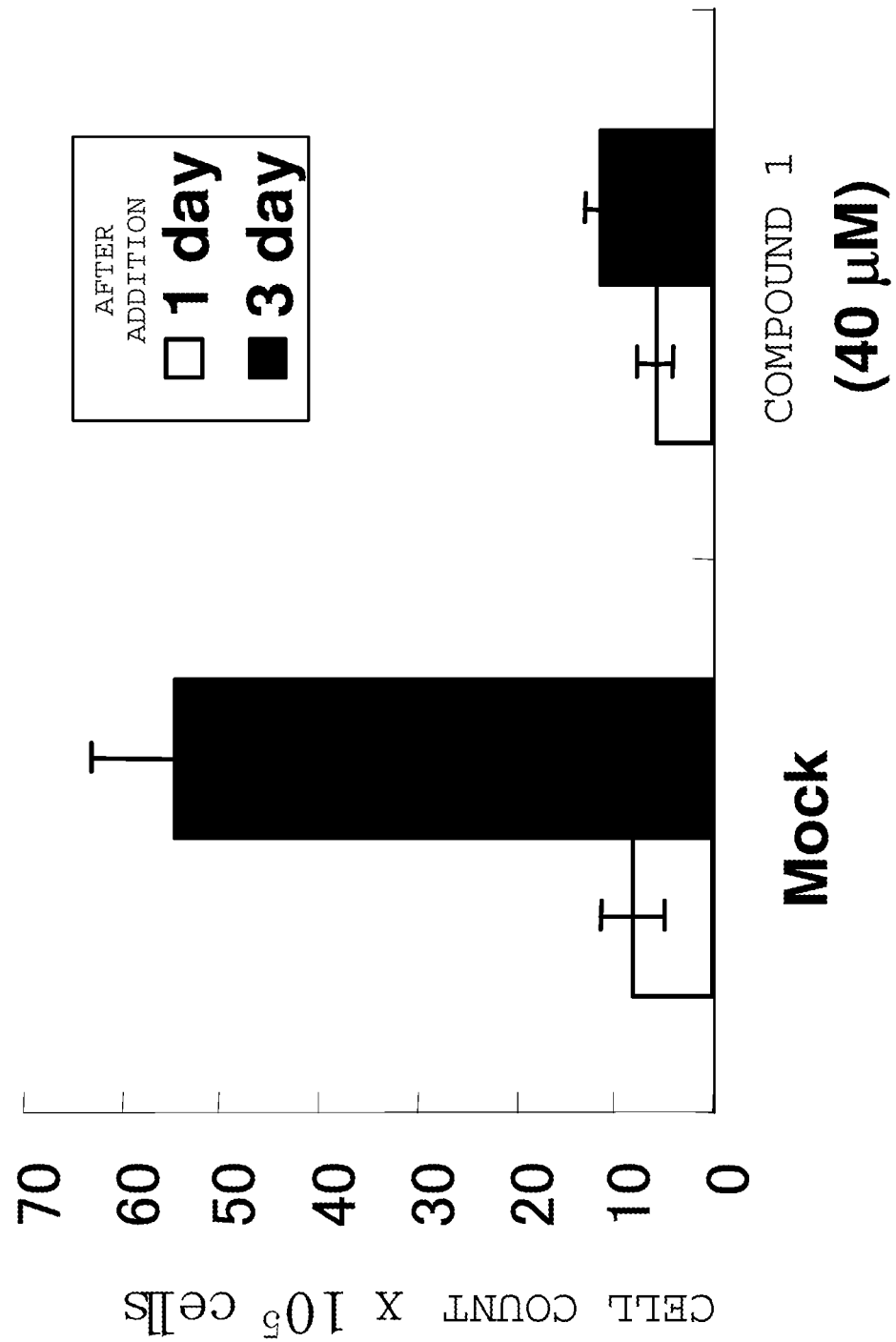

PROTEIN PHOSPHATASE INHIBITOR

This application is a U.S. National Phase under 35 U.S.C. §371 of International Application PCT/JP2009/005128, filed on Oct. 2, 2009, which claims priority to Japanese Patent Application No. 2008-262646, filed on Oct. 9, 2008. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a novel protein phosphatase inhibitor and a medicine containing the same.

BACKGROUND ART

A protein phosphatase is an enzyme dephosphorylating a phosphoprotein, and is said to act on the regulation of glucose metabolism, smooth muscle contraction, cell cycle, DNA replication, transcription, translation, cell adhesion, activation and differentiation of cells, etc. in the living body and the maintenance of the immune system and the nervous system of the living body. Accordingly, a protein phosphatase inhibitor has potential to be utilized as various medicines, and thus is widely explored. Among protein phosphatases, a serine/threonine phosphatase (Ser/Thr phosphatase) is classified into four families, PP1, PP2A, PP2B, and PP2C (PPM1), based on its chemical properties and gene structures. The PPM1 family is particularly involved in the regulation of cellular functions such as DNA repair mechanism, stress response, signal transduction, and cell proliferation, and thus the development of an inhibitor of the PPM1 family is particularly gaining attention.

Protein Phosphatase Magnesium-Dependent 1, Delta (PPM1D), belonging to the PPM1 family, is a phosphatase which is induced in a manner dependent on p53, a tumor suppressor protein, and increases in a cell once DNA is damaged by an ultraviolet ray, an electromagnetic ray, and the like. PPM1D is reported to be overly expressed in a plurality of cancer cells including breast cancer (Non Patent Document 1), drawing the attention to the relationship between carcinogenesis and PPM1D. Meanwhile, it is suggested that PPM1D is constitutively expressed in the living body, and based on the studies using knockout mice, PPM1D is involved in not only carcinogenesis but also spermatogenesis, aging, and immune response (Non Patent Document 2).

As described above, despite the fact that some of the protein phosphatases, for example PPM1D, play an important role in carcinogenesis and other phenomena, very little is known about their functions and inhibitors.

Non Patent Document 1: Nat. Genet., 31, 210 to 215, 2002
Non Patent Document 2: Mol. Cell. Biol., 22, 1094 to 1105, 2002

DISCLOSURE OF THE INVENTION

Problems to be Solved by the Invention

It is an object of the present invention to provide a novel protein phosphatase inhibitor.

Means for Solving the Problems

In view of the foregoing, the present inventors synthesized low molecular weight compounds and evaluated them for their protein phosphatase-inhibitory activities, in consideration of factors such as the possibility of oral administration and the immunogenicity when administered as a medicine. As a result, they have found that a silicon compound represented by the following general formula (1) has an excellent protein phosphatase-inhibitory activity, particularly a PPM1D-inhibitory activity, with its inhibitory activity more selective for PPM1D than for an analogous phosphatase PPM1A, a p38-dependent phosphatase. They have also found that this silicon compound exhibits its inhibitory effect in cancer cells and also exerts an excellent inhibitory effect on cancer cell proliferation. Based on the above findings, they have found this silicon compound useful as a therapeutic drug for malignant tumor, thereby completing the present invention.

That is, the present invention is to provide a protein phosphatase inhibitor containing, as an active ingredient, a silicon compound represented by the general formula (1) or a salt thereof:

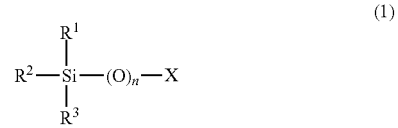

(1)

wherein $R^1$, $R^2$, and $R^3$ are the same or different and represent a hydrocarbon group having 1 to 12 carbon atoms; X represents an optionally substituted hydrocarbon group having 3 to 36 carbon atoms or an optionally substituted heterocyclic group; and n represents an integer of 0 or 1.

The present invention further provides a medicine containing a compound represented by the aforementioned general formula (1) or a salt thereof.

The present invention further provides use of a compound represented by the aforementioned general formula (1) or a salt thereof for the production of a protein phosphatase inhibitor.

The present invention further provides use of a compound represented by the aforementioned general formula (1) or a salt thereof for the production of a medicine.

The present invention further provides a method for inhibiting a protein phosphatase including administering a compound represented by the aforementioned general formula (1) or a salt thereof.

The present invention further provides a method for treating malignant tumor including administering a compound represented by the aforementioned general formula (1) or a salt thereof.

Effects of the Invention

The compound represented by the general formula (1) of the present invention (hereinbelow, also referred to as the compound of the present invention (1)) or a salt thereof selectively inhibits PPM1D, which is a phosphatase dependent on p53, a tumor suppressor gene, and suppresses proliferation of cancer cells, thus is useful as a medicine as represented by a therapeutic drug for malignant tumor. Further, because the compound of the present invention (1) or a salt thereof is a low molecular weight compound, there is no problem of, for

BRIEF DESCRIPTION OF THE DRAWINGS

FIG. 4 is a diagram showing the effect of the compound of Example 1 (Compound (1)) on breast cancer-derived MCF7 cells three days after addition of the compound as observed under the microscope. The pictures on the right are enlarged pictures of the area surrounded by a black box on the left; and FIG. 5 is a diagram showing the effect of the compound of Example 1 (Compound (1)) on cell proliferation of breast cancer-derived MCF7 cells. The cell count one day and three days after addition of the compound was measured.

MODE FOR CARRYING OUT THE INVENTION

Figure 1:
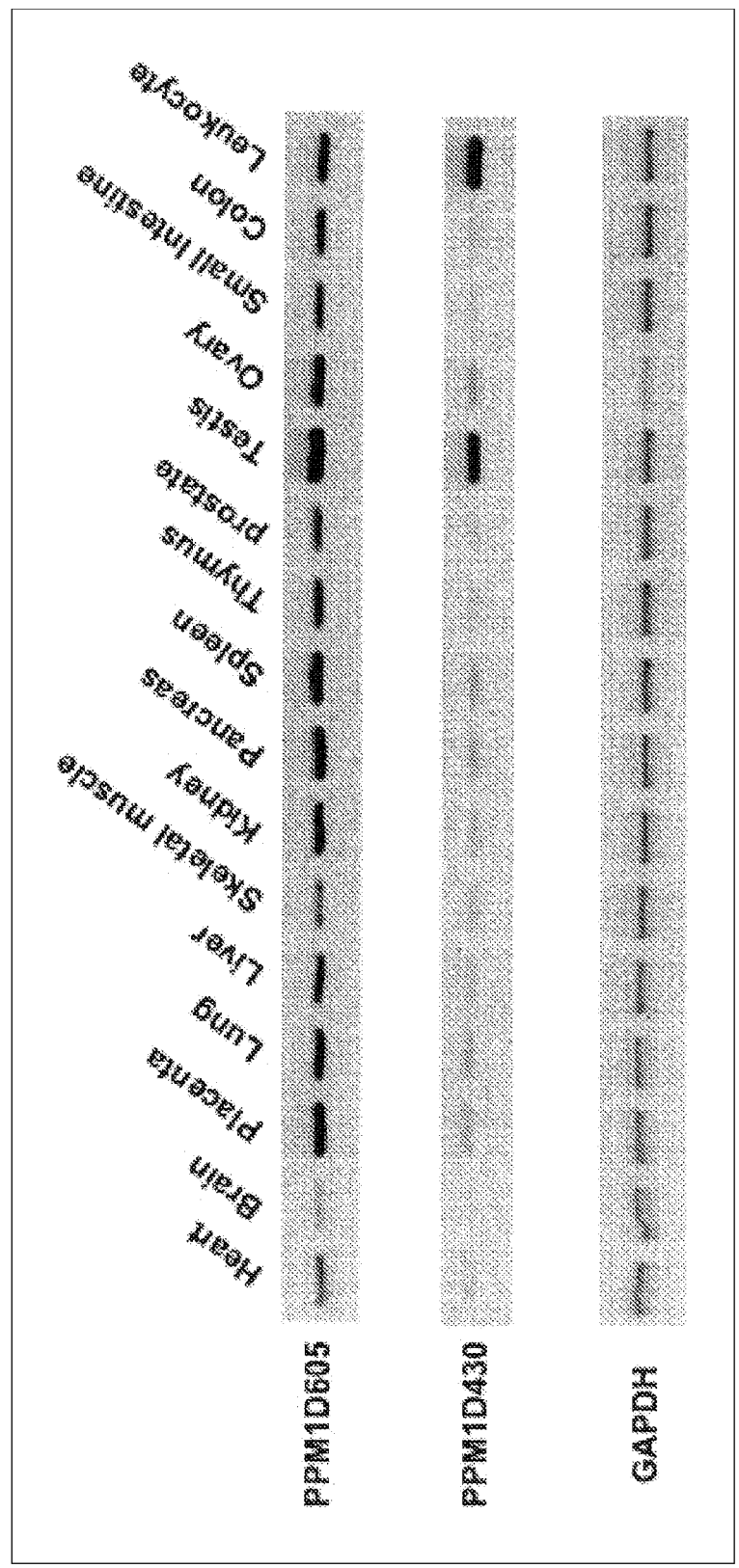
FIG. 1 is a diagram showing the expression levels of two PPM1D isoforms, PPM1D605 and PPM1D430, in various organs.

In the general formula (1), $R^1$, $R^2$, and $R^3$ are the same or different and can be a hydrocarbon group having 1 to 12 carbon atoms. Examples of the hydrocarbon group include a linear, branched, or cyclic saturated or unsaturated hydrocarbon group. Further, a linear, branched, or cyclic alkyl group, aralkyl group, or aromatic hydrocarbon group is preferable. Furthermore, a linear or branched alkyl group having 1 to 8 carbon atoms, an aromatic hydrocarbon group having 6 to 14 carbon atoms, or a $C_{6-10}$ aryl-$C_{1-6}$ alkyl group is preferable. In more detail, an alkyl group having 1 to 6 carbon atoms such as a methyl group, an ethyl group, an n-propyl group, an isopropyl group, an n-butyl group, a sec-butyl group, an isobutyl group, and a tert-butyl group is preferable. Also, an aryl group having 6 to 10 carbon atoms such as a phenyl group and a naphthyl group is preferable. Furthermore, a phenyl-$C_{1-4}$ alkyl group such as a benzyl group and phenethyl group is preferable. The substituents $R^1$, $R^2$, and $R^3$ on the silyl group may be the same or different.

Specific examples of $(R^1)(R^2)(R^3)Si$— include a trimethylsilyl group, a triethylsilyl group, a tri(n-propyl)silyl group, a triisopropylsilyl group, a tri(n-butyl)silyl group, a tri(sec-butyl)silyl group, a triisobutylsilyl group, a tert-butyldimethylsilyl group, a dimethylphenylsilyl group, a methyldiphenylsilyl group, a triphenylsilyl group, and a tert-butyldiphenylsilyl group.

In the general formula (1), X represents an optionally substituted hydrocarbon group having 3 to 36 carbon atoms or an optionally substituted heterocyclic group. Here, the hydrocarbon group having 3 to 36 carbon atoms may be linear, branched, or cyclic hydrocarbon, and it may be saturated or unsaturated. More preferably, it is a linear, branched, or cyclic hydrocarbon group having 3 to 24 carbon atoms.

Examples of the hydrocarbon group include a $C_3$-$C_{24}$ alkyl group, a $C_{3-24}$ alkenyl group, a $C_{3-24}$ alkynyl group, and a saturated or unsaturated hydrocarbon group having a $C_3$-$C_{24}$ cyclic structure. Preferred examples of the $C_3$-$C_{24}$ alkyl group include a $C_3$-$C_6$ alkyl group such as an n-propyl group, an isopropyl group, an n-butyl group, a sec-butyl group, an isobutyl group, an n-pentyl group, and an n-hexyl group. The $C_{3-24}$ alkenyl group is preferably a $C_3$-$C_8$ alkenyl group such as a 1-propene-1-yl group, a 2-propene-1-yl group, an isopropenyl group, a 1-butene-1-yl group, a 2-butene-1-yl group, a 3-butene-1-yl group, a 1-butene-2-yl group, a 2-butene-2-yl group, and a 3-butene-2-yl group. The $C_{3-24}$ alkynyl group is preferably a $C_3$-$C_8$ alkynyl group such as a propynyl group, a pentynyl group, a hexynyl group, and an octynyl group.

Examples of the saturated or unsaturated hydrocarbon group having a $C_3$-$C_{24}$ cyclic structure include a hydrocarbon group with a cyclic structure having one to three 5 or 6-membered cyclic saturated or unsaturated hydrocarbon(s).

These hydrocarbon groups may have one to four substituent(s) selected from the group consisting of a hydroxyl group, a nitrile group, a carboxyl group, an alkoxycarbonyl group, a cyano group, an alkoxy group, an alkylthio group, a substituted sulfonyl group, a halogen atom, a tri-substituted silyl group, and a tri-substituted silyloxy group. Here, the number of carbon atoms of the alkoxy group and the alkylthio group is preferably 1 to 6, and that of the alkoxycarbonyl group is preferably 2 to 7. Also, the tri-substituted silyl group or the tri-substituted silyloxy group is preferably the aforementioned $(R^1)(R^2)(R^3)Si$—$(O)_n$-group. Examples of the substituted sulfonyl group include a $C_{1-4}$ alkanesulfonyl group such as a methanesulfonyl group, a benzenesulfonyl group, and a toluenesulfonyl group. These hydrocarbon groups may have one to four of these substituent(s).

Examples of the heterocyclic group represented by X include a 5 or 6-membered heterocyclic group having a nitrogen atom or an oxygen atom, and specific examples thereof include a pyrrolyl group, a pyrrolidinyl group, a pyridyl group, a furanyl group, a tetrahydrofuranyl group, a pyranyl group, and a tetrahydropyranyl group.

The heterocyclic group may have one to five substituent(s) selected from an aryl group, an aralkyl group, an alkyl group, an amino group, an alkylamino group, an alkenylamino group, an acyloxy group, and an aralkyloxy group. Examples of the aryl group include a phenyl group and a naphthyl group. Examples of the aralkyl group include a benzyl group and a phenethyl group. Examples of the alkyl group include an alkyl group having 1 to 6 carbon atoms such as a methyl group and an ethyl group. Examples of the alkylamino group include an alkylamino group having 1 to 6 carbon atoms such as a methylamino group and an ethylamino group. Examples of the alkenylamino group include a propenylamino group and a 2-methylene-propylamino group. Examples of the acyloxy group include an acetoxy group and a propionyloxy group. Examples of the aralkyloxy group include a benzyloxy group.

Preferred examples of the compound of the present invention (1) include the ones represented by the following formulas (2) to (8):

(2)

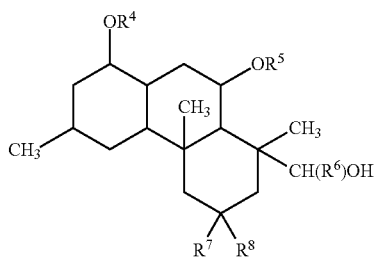

wherein $R^4$, $R^5$, $R^6$, and $R^8$ are as defined above; and (3)

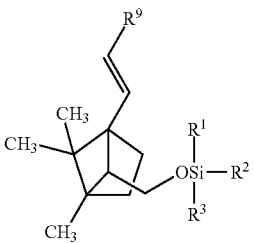

wherein $R^9$ represents a hydroxymethyl group, a carboxyl group, or an alkoxycarbonyl group, and $R^1$, $R^2$, and $R^3$ are as defined above.

Among the compounds of the formula (3), preferred configurations are as follows:

wherein $R^4$ and $R^5$ are the same or different and represent a hydrogen atom or $(R^1)(R^2)(R^3)Si$—, wherein at least one of $R^4$ and $R^5$ is $(R^1)(R^2)(R^3)Si$—;

$R^6$ represents a hydrogen atom or may form —O-(ether bond) together with the hydroxyl group of $R^8$; and $R^7$ represents a hydrogen atom and $R^8$ represents a hydroxyl group, or $R^7$ and $R^8$ may together form an oxo group (=O).

The compound of the present invention (2) contains multiple asymmetric carbon atoms, and thus it could exist in multiple optically active forms or a mixture thereof. Preferred configurations of the compound of the present invention (2) are as follows:

(3-1)

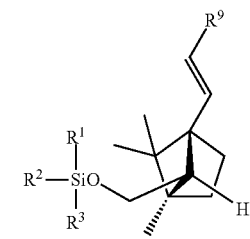

(2-1)

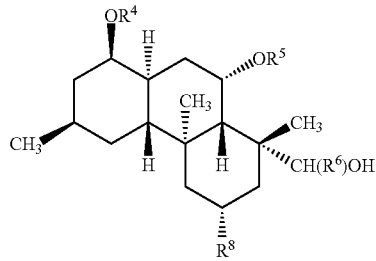

(3-2)

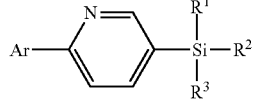

(2-2)

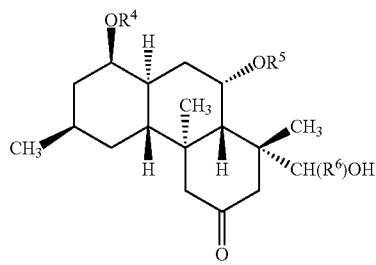

wherein $R^1$, $R^2$, $R^3$, and $R^9$ are as defined above; and (4)

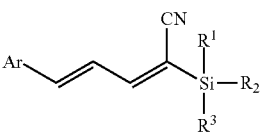

(5)

(6)

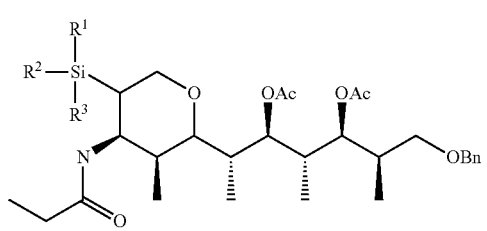

(2-3)

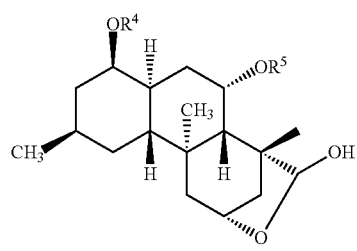

-continued

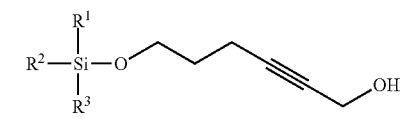

(7)

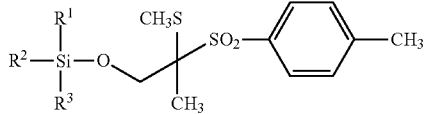

(8)

wherein Ar represents an aryl group (for example, a phenyl group), and $R^1$, $R^2$, and $R^3$ are as defined above.

The compound of the present invention (1) may form a salt. Examples of a salt-forming acid or base include a mineral acid such as hydrochloric acid and sulfuric acid; an organic acid such as acetic acid, succinic acid, and citric acid; an alkali metal such as sodium and potassium; and an alkaline earth metal such as calcium and magnesium. Further, the compound of the present invention (1) may be in the form of a hydrate and the like.

The compound of the present invention (1) is characterized in that it has $(R^1)(R^2)(R^3)Si(O)_n$— in its structure. A compound lacking this structure is virtually devoid of a protein phosphatase-inhibitory effect, particularly a PPM1D-inhibitory effect.

The compound of the present invention (1) can be produced according to, for example, the following reaction formulas:

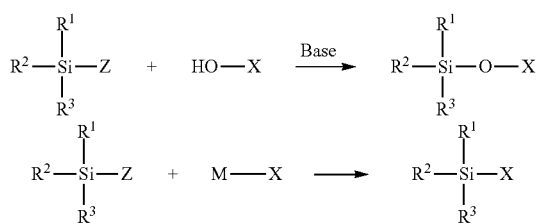

wherein Z represents a leaving group, M represents a metal atom, and $R^1$, $R^2$, $R^3$, and X are as defined above.

A silicon compound having a leaving group Z $((R^1)(R^2)(R^3)Si$—Z) is reacted with an alcohol or a phenol (HO—X) in the co-presence of a base to give $(R^1)(R^2)(R^3)Si$—OX. Alternatively, a silicon compound having a leaving group Z $((R^1)(R^2)(R^3)Si$—Z) is reacted with an organic metal compound (M-X) to give $(R^1)(R^2)(R^3)Si$—X.

In the formula, no particular limitation is imposed on the leaving group Z, and examples thereof include a chloro group, a bromo group, an iodine group, a sulfonate group, an alkylsulfonate group, an arylsulfonate group, or a perchlorate group. Examples of the base include trialkylamine, dialkylarylamine, sodium hydride, methyllithium, or n-butyllithium. M represents a metal ion, desirably, an alkali metal or an alkaline earth metal such as lithium, sodium, potassium, or magnesium.

The compound of the present invention (1) or a salt thereof obtained as above has a cancer cell proliferation-inhibitory action and a protein phosphatase-inhibitory activity, particularly a potent PPM1D-inhibitory activity. Further, it also exerts its inhibitory activity on PPM1D in cells (particularly, in cancer cells). Also, PPM1D is known to be induced in a manner dependent on p53, a tumor suppressor gene. Meanwhile, PPM1A, a Ser/Thr phosphatase as PPM1D is, is said to be p38-dependent. The compound of the present invention (1) is characterized in that it specifically inhibits PPM1D, while hardly acting on PPM1A. Accordingly, the compound of the present invention (1) or a salt thereof is useful as a therapeutic drug for malignant tumor.

Furthermore, as the compound of the present invention (1) is a low molecular weight compound, it is not immunogenic and can be administered orally. Thus, it is useful as a medicine for mammals including humans also from the viewpoint of the safety and the compliance.

When including the compound of the present invention (1) or a salt thereof in a pharmaceutical composition, it can be mixed with pharmaceutically acceptable carriers as needed, and prepared into various dosage forms depending on the preventive or therapeutic purpose. Examples of the dosage form include an oral agent, an injection, a suppository, an ointment, and a patch, among which an oral agent is preferable. Each of these dosage forms can be produced by a publicly known production method routinely employed by those skilled in the art.

As the pharmaceutically acceptable carrier, an excipient, a binder, a disintegrant, a lubricant, and a colorant in a solid preparation; a solvent, a solubilizing aid, a suspending agent, an isotonic agent, a buffer, and a soothing agent in a liquid preparation, and the like are used. Further, a pharmaceutical aid such as a preservative, an antioxidant, a colorant, a sweetener, and a stabilizer can also be used as needed.

When preparing an oral solid preparation, an excipient, and if needed, a binder, a disintegrant, a lubricant, a colorant, a flavoring agent, an odor-masking agent, and the like can be added to the compound of the present invention, and then a tablet, a coated tablet, a granule, a powder, a capsule, and the like can be produced by an ordinary method.

When preparing an oral liquid preparation, a taste-masking agent, a buffer, a stabilizer, an odor-masking agent, and the like can be added to the compound of the present invention, and then an internal liquid agent, a syrup, an elixir, and the like can be produced by an ordinary method.

When preparing an injection, a pH adjuster, a buffer, a stabilizing agent, an isotonic agent, a local anesthetic, and the like can be added to the compound of the present invention, and then injections for subcutaneous, intramuscular, and intravenous administration can be produced by an ordinary method.

A suppository can be prepared by adding a pharmaceutical carrier publicly known in the art, for example, polyethylene glycol, lanolin, cacao butter, and fatty acid triglyceride to the compound of the present invention, and then applying an ordinary production method.

When preparing an ointment, a normally-used base, stabilizer, humectant, preservative, and the like are added to the compound of the present invention as needed. The resulting mixture is then mixed and prepared into an ointment by an ordinary method.

When preparing a patch, the aforementioned ointment, a cream, a gel, a paste, and the like may be spread over a normal base by an ordinary method.

The content of the compound of the present invention in each of the aforementioned preparations varies depending on the symptoms of a patient, the dosage form, and the like; however, normally, the content in an oral agent is approximately 0.05 to 1000 mg, the content in an injection is approximately 0.01 to 500 mg, and the content in a suppository is approximately 1 to 1000 mg.

Also, the daily doses of these preparations vary depending on the symptoms, body weight, age, sex, and the like of a patient, and thus cannot be flatly determined; however, normally, the daily dose of an adult (a body weight of 60 kg) is approximately 0.05 to 5000 mg, preferably 0.1 to 1000 mg, and the daily dose is preferably administered once a day or divided into approximately two to three portions a day.

Examples of the disease that can be treated by administration of a medicine containing the compound of the present invention include malignant tumor. Examples thereof include head and neck cancer, esophageal cancer, gastric cancer, colon cancer, rectal cancer, liver cancer, gallbladder and bile duct cancer, pancreatic cancer, lung cancer, breast cancer, ovary cancer, uterine cervical cancer, uterine cancer, renal cancer, bladder cancer, prostate cancer, testicular tumor, osteosarcoma soft tissue sarcoma, leukemia, malignant lymphoma, multiple myeloma, skin cancer, and brain tumor.

As will be shown in the following Examples, the present inventors identified PPM1D430, a selective splicing variant of human PPM1D consisting of 430 residues, at mRNA and protein levels, revealing that PPM1D430 is specifically expressed in leukocytes and the testis (FIG. 1).

It is to be noted that PPM1D605 in FIG. 1 corresponds to one that has been conventionally expressed as PPM1D. In order to prevent it from being mixed up with a novel isoform PPM1D430, conventional PPM1D is expressed as PPM1D605 here. Based on the observation that the immune response of B cells and T cells to antigen stimulation is attenuated in a PPM1D-deficient mouse (Non Patent Document 2), a PPM1D inhibitor is useful as an immunosuppressant, and the compound of the present invention is useful also as an immunosuppressant in organ transplantation.

Further, as PPM1D is known to activate an estrogen receptor and a progesterone receptor (J. Biol. Chem., 281, 7089 to 7101, (2005)), the compound of the present invention is useful also as an anti-hormone drug.

EXAMPLES

Hereinbelow, the present invention will be explained further in detail with reference to Examples and Test Examples. However, the present invention is not limited to these Examples.

Example 1

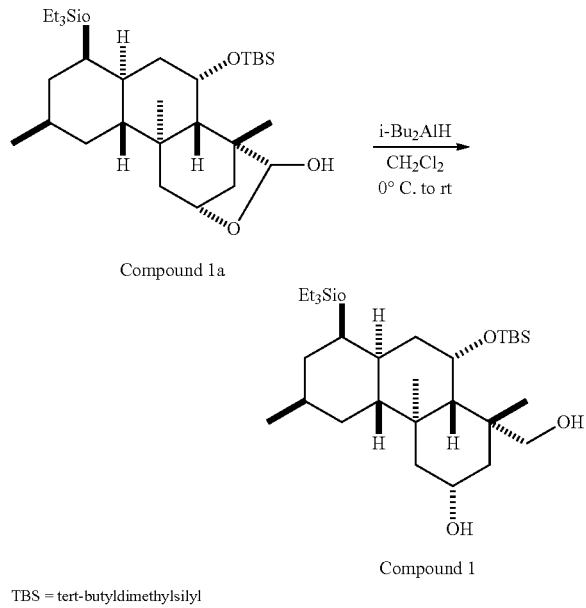

Compound 1

TBS = tert-butyldimethylsilyl
Et = ethyl, Bu = butyl

A 5 mL test tube was charged with Compound 1a (11.5 mg, 21.3 μmol) (Miyashita, M. et al., Science 2004, 305, 495; Yoshimura, F. et al., Chem. Eur. J. 2009, 15, 6626) and purged with argon, and then Compound 1a was dissolved in dry dichloromethane (0.21 mL). After cooling the resulting mixture to 0° C., diisobutylaluminum hydride (a 1.0 M hexane solution, 107 μL, 0.107 mmol) was added. After stirring at room temperature for two hours, diisobutylaluminum hydride (a 1.0 M hexane solution, 107 μL, 0.107 mmol) was added, followed by stirring for further 3.5 hours. Ethyl acetate (0.1 mL) was slowly added to terminate the reaction. After diluting the resulting mixture with ethyl acetate, a saturated aqueous solution of ammonium chloride and potassium sodium tartrate tetrahydrate were added, followed by vigorous stirring until the disappearance of white precipitates. The resulting mixture was extracted with ethyl acetate and dichloromethane, and then dried over anhydrous magnesium sulfate. After removing the solvent, the resulting crude product was purified by flash column chromatography (silica gel, hexane/ethyl acetate=7/1 to 5/1) to give Compound 1 as a colorless crystal (10.5 mg, 91%).

Compound 1: $^1$H-NMR (500 MHz, CDCl$_3$) δ 0.09 (3H, s), 0.13 (3H, s), 0.59 (6H, q, J=7.5 Hz), 0.92 (9H, s), 0.96 (9H, t, J=8.0 Hz), 1.03 (3H, s), 1.11 (3H, d, J=6.9 Hz), 1.32 (3H, s), 1.25-1.42 (4H, m), 1.45-1.68 (6H, m), 1.77-1.83 (1H, m), 1.95-2.08 (3H, m), 3.72-3.76 (1H, m), 3.72 (1H, d, J=12.0 Hz), 3.98 (1H, d, J=11.5 Hz), 4.10 (1H, quintet, J=4.0 Hz), 4.54 (1H, brs).

Example 2

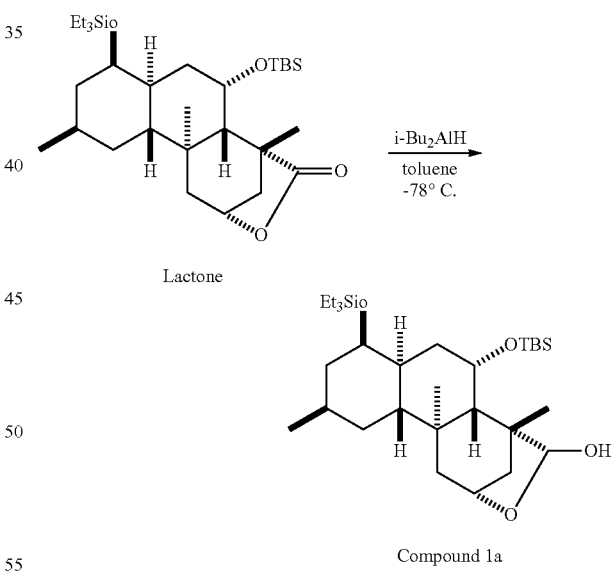

Compound 1a

TBS = tert-butyldimethylsilyl
Et = ethyl, Bu = butyl

A 100 mL two-necked recovery flask was charged with lactone (1.0 g, 1.88 mmol) (Miyashita, M. et al., Science 2004, 305, 495) and purged with argon, followed by addition of dry toluene (18 mL). After cooling to −78° C., diisobutylaluminum hydride (a 1.01 M toluene solution, 1.86 mL, 1.88 mmol) was added, followed by stirring at −78° C. for two hours. Ethyl acetate was then slowly added at −78° C. to terminate the reaction. Water and potassium sodium tartrate tetrahydrate were then added, followed by vigorous stirring at room temperature until the disappearance of white precipitates. The resulting mixture was extracted with ethyl acetate, washed with saturated brine, and then dried over anhydrous magnesium sulfate. After removing the solvent, the resulting crude product was purified by flash column chromatography (silica gel, hexane/ethyl acetate=9/1 to 4/1 to 3/1) to give Compound 1a as a colorless oily product (608.5 mg, 60%), from which 313.7 mg (0.584 mmol, 31%) of the raw material lactone was recovered. The same operation was repeated twice on the lactone thus collected, whereby further 250.9 mg (25%) of Compound 1a was obtained.

Example 3

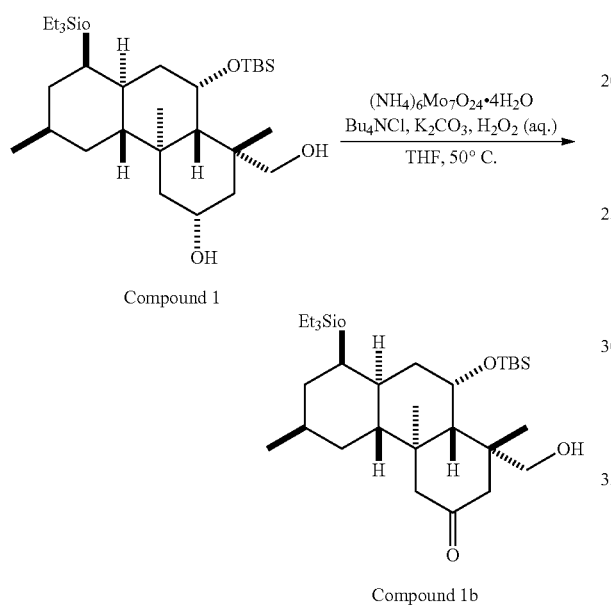

Compound 1b

TBS = tert-butyldimethylsilyl
Et = ethyl, Bu = butyl, THF = tetrahydrofuran

In a 5 mL test tube, Compound 1 (4.0 mg, 7.4 mmol) was placed and dissolved in tetrahydrofuran (0.15 mL). After that, potassium carbonate (2.0 mg, 15 μmol), tetrabutylammonium chloride (4.1 mg, 15 μmol), hexaammonium heptamolybdate tetrahydrate (9.1 mg, 7.4 μmol), and hydrogen peroxide water (35%, 37 μL) were sequentially added. The resulting mixture was stirred at room temperature for one minute, and then at 50° C. for 2.5 hours. The mixture was cooled to room temperature and then diluted with water. The resulting mixture was extracted with ethyl acetate and dichloromethane, and then dried over anhydrous magnesium sulfate. After removing the solvent, the resulting crude product was purified by flash column chromatography (silica gel, hexane/ethyl acetate=3/1) to give Compound 1b as a colorless oily product (3.8 mg, 95%).

Compound 1b: $^1$H-NMR (500 MHz, CDCl$_3$) δ 0.13 (3H, s), 0.17 (3H, s), 0.55-0.63 (6H, m), 0.94 (9H, s), 0.97 (9H, t, J=8.0 Hz), 1.12 (3H, s), 1.12 (3H, d, J=7.5 Hz), 1.17 (3H, s), 1.27-1.42 (2H, m), 1.50-1.71 (7H, m), 1.97-2.07 (1H, m), 2.04 (1H, d, J=14.9 Hz), 2.12 (1H, d, J=13.8 Hz), 2.40 (1H, d, J=14.9 Hz), 2.64 (1H, d, J=14.3 Hz), 3.54 (1H, d, J=12.0 Hz), 3.58 (1H, d, J=12.0 Hz), 3.75-3.80 (1H, m), 4.48 (1H, d, J=1.8 Hz).

Example 4

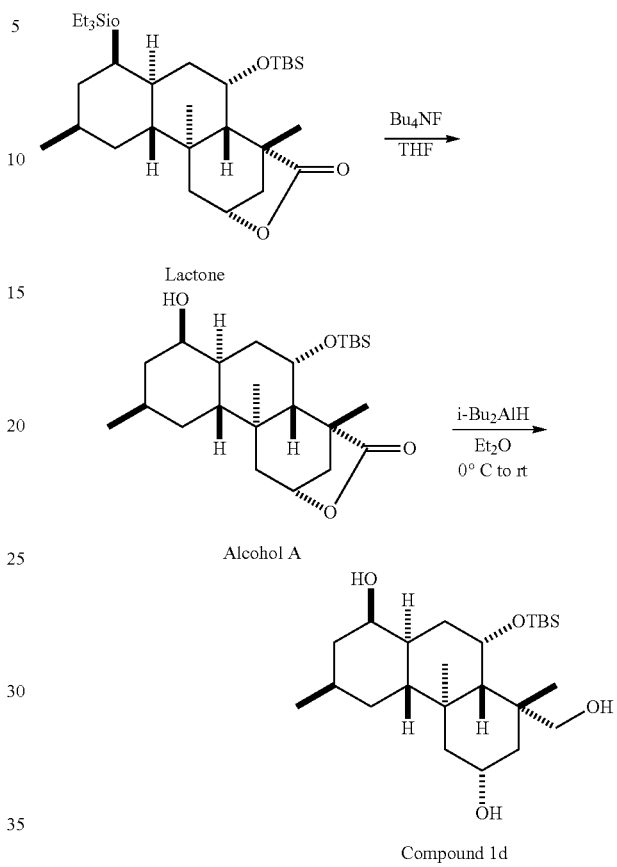

Compound 1d

TBS = tert-butyldimethylsilyl
Et = ethyl, Bu = butyl, THF = tetrahydrofuran

A 5 mL test tube was charged with lactone (6.3 mg, 11.7 μmol) (Miyashita, M. et al., Science 2004, 305, 495) and purged with argon, and then lactone was dissolved in dry tetrahydrofuran (0.1 mL). After cooling the resulting mixture to 0° C., tetrabutylammonium fluoride (a 1.0 M tetrahydrofuran solution, 23.5 μL, 23.5 μmol) was added, followed by stirring at room temperature for two hours. Tetrabutylammonium fluoride (a 1.0 M tetrahydrofuran solution, 8 μL, 8 μmol) was added, followed by stirring at room temperature for further 1.5 hours. The reaction was terminated with a saturated aqueous solution of ammonium chloride, and the resulting mixture was extracted with ethyl acetate. The mixture was then dried over anhydrous magnesium sulfate, and the solvent was removed. The resulting crude product was then purified by flash column chromatography (silica gel, hexane/ethyl acetate=8/1 to 2/1) to give Alcohol A as a colorless oily product (5.5 mg). A 5 mL test tube was charged with the Alcohol A thus obtained (5.5 mg) and purged with argon. Alcohol A was then dissolved in dry diethyl ether (0.12 mL), followed by cooling to 0° C. After addition of diisobutylaluminum hydride (a 1.02M hexane solution, 57 μL, 58.5 μmol), the resulting mixture was stirred at room temperature for 2.5 hours. Ethyl acetate (30 μL) was slowly added at 0° C. to terminate the reaction. After diluting the mixture with ethyl acetate, a saturated aqueous solution of ammonium chloride and potassium sodium tartrate tetrahydrate were added, followed by vigorous stirring until the disappearance of white precipitates. The resulting mixture was extracted with ethyl acetate, and then dried over anhydrous magnesium sulfate. After removing the solvent, the crude product was purified by flash column chromatography (silica gel, hexane/ethyl acetate=1/2) to give Compound 1d as a colorless crystal (3.8 mg, 76% for 2 steps).

Compound 1d: $^1$H-NMR (500 MHz, CDCl$_3$) δ 0.11 (3H, s), 0.13 (3H, s), 0.92 (9H, s), 1.02 (3H, s), 1.15 (3H, d, J=7.5 Hz), 1.19 (1H, s), 1.23-1.29 (1H, m), 1.35 (3H, s), 1.36-1.41 (3H, m), 1.50-1.55 (1H, m), 1.65-1.85 (7H, m), 2.03-2.10 (2H, m), 3.69 (1H, d, J=11.5 Hz), 3.79 (1H, brs), 4.04 (1H, d, J=11.5 Hz), 4.11 (1H, quintet, J=4.0 Hz), 4.57 (1H, brs).

Example 5

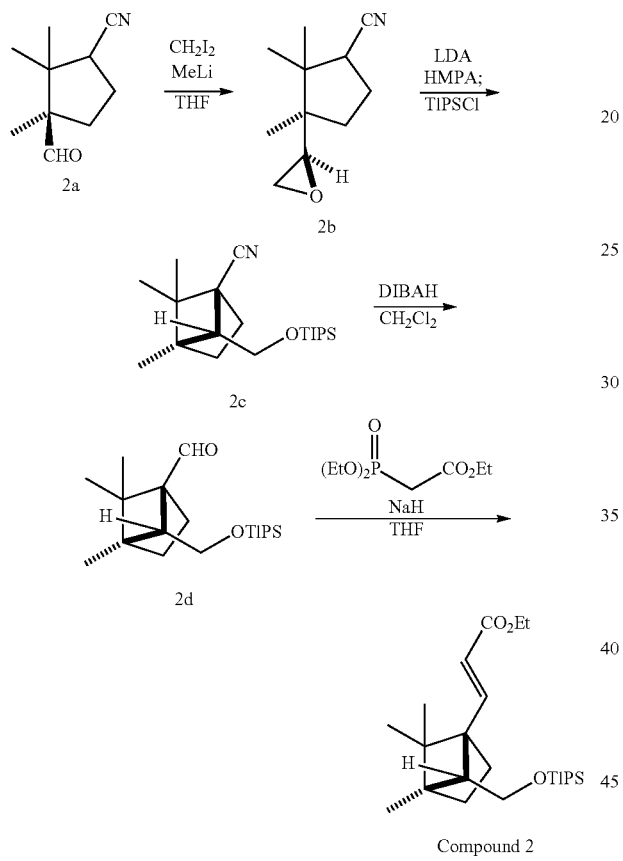

Synthesis of Compound 2b: a known compound, Compound 2a (2.91 g, 17.6 mmol), and diiodomethane (3.0 mL, 37.8 mL) were dissolved in tetrahydrofuran (80 mL), and then cooled to −78° C. Methyllithium (a 1.04 M diethyl ether solution, 42.3 mL, 44.0 mmol) was added, followed by stirring at −78° C. for 20 minutes. A saturated aqueous solution of sodium bicarbonate was added to terminate the reaction, followed by extraction with ethyl acetate. The resulting organic layer was washed with saturated brine and then dried over anhydrous magnesium sulfate. After concentration, the resulting residue was purified by silica gel column chromatography (hexane/ethyl acetate=8:1) to give Compound 2c (2.12 g, 59%).

Synthesis of Compound 2c: a solution of lithium diisopropylamide in tetrahydrofuran (22 mL) was prepared from diisopropylamine (2.9 mL, 28.0 mmol) and butyllithium (a 1.59 M hexane solution, 14.6 mL, 23.2 mmol), and cooled to −78° C., to which a mixed solution of Compound 2b (2.08 g, 11.6 mmol) in tetrahydrofuran (36 mL)-hexamethylphosphoramide (16 mL, 93.0 mmol) was added. The resulting mixture was stirred at 0° C. for two hours, to which chlorotriisopropylsilane (6.2 mL, 29.0 mmol) was added. After stirring at room temperature for 30 minutes, a saturated aqueous solution of ammonium chloride was added to terminate the reaction. After extraction with hexane, the resulting organic layer was dried over anhydrous magnesium sulfate. After concentration, the resulting residue was purified by silica gel column chromatography (hexane/ethyl acetate=50:1) to give Compound 2c (3.51 g, 89%).

Synthesis of Compound 2: Compound 2c (3.60 g, 10.6 mmol) was dissolved in dichloromethane (53 mL), to which diisobutylaluminum hydride (a 0.98 M hexane solution, 21.6 mL, 21.2 mmol) was added at −78° C. After stirring at room temperature for two hours, tetrahydrofuran and a 10% aqueous solution of tartaric acid were added to terminate the reaction. After stirring at 40° C. for 20 minutes, the mixture was extracted with hexane. The resulting organic layer was washed with saturated brine, dried over anhydrous magnesium sulfate, and then concentrated. Aldehyde obtained as the crude product was directly used in the following reaction. Sodium hydride (936.6 mg, 21.2 mmol) was added to a solution of diethylphosphonoethyl acetate (6.3 mL, 31.7 mmol) in tetrahydrofuran (16 mL) at 0° C., followed by stirring (hereinbelow, referred to as Solution A). Solution A was added to a solution of the aldehyde thus obtained (10.6 mmol) in tetrahydrofuran at 0° C. After stirring at room temperature for 20 minutes, a saturated aqueous solution of ammonium chloride was added to terminate the reaction. After extraction with hexane, the resulting organic layer was washed with saturated brine, and then dried over anhydrous magnesium sulfate. After concentration, the resulting residue was purified by silica gel column chromatography (hexane/ethyl acetate=18:1) to give Compound 2 (3.93 g, 71% for 2 steps).

Compound 2: $^1$H-NMR (500 MHz, CDCl$_3$) δ 6.96 (1H, d, J=16.0 Hz), 5.86 (1H, d, J=16.0 Hz), 4.18 (2H, m), 3.53 (2H, d, J=6.3 Hz), 2.27 (1H, t, J=6.3 Hz), 1.72 (2H, m), 1.60-1.50 (2H, m), 1.43 (1H, m), 1.27 (3H, t, J=9.8 Hz), 1.10-1.04 (24H, m), 0.94 (3H, s), 0.74 (3H, s).

Example 6

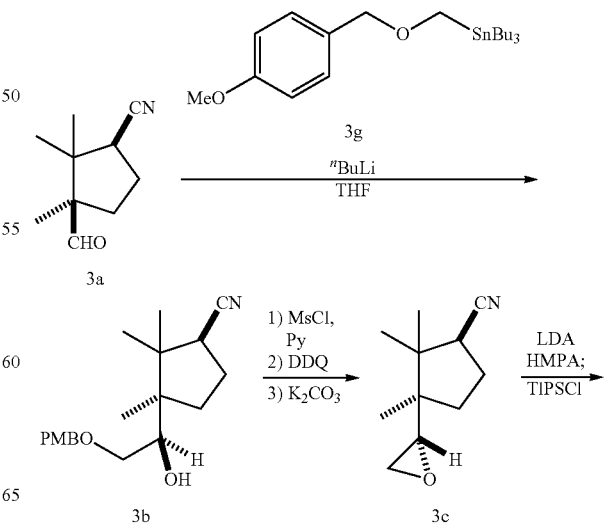

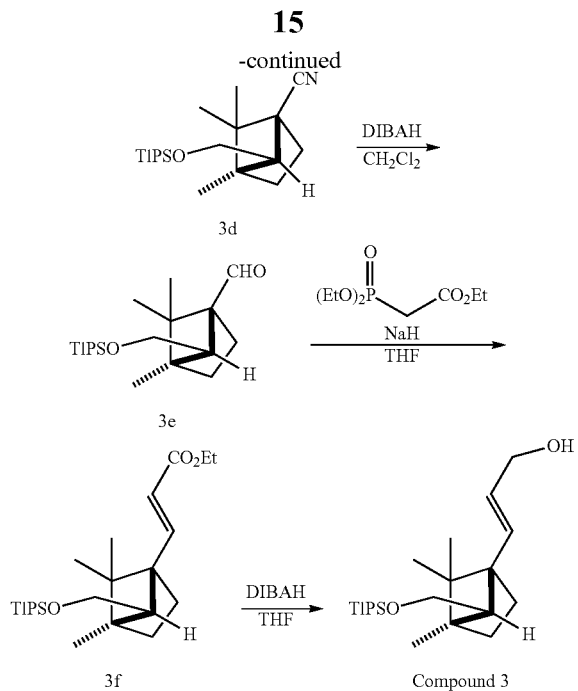

Synthesis of Compound 3b: butyllithium (a 2.64 M hexane solution, 5.7 mL, 15.0 mmol) was added to a solution of 38 g of α-stannyl ether (7.09 g, 16.0 mmol) in tetrahydrofuran (20 mL) at −78° C. After stirring at −78° C. for 20 minutes, the resulting mixture was cooled to −100° C. A solution of a known compound, Compound 3a (1.66 g, 10 mmol), in tetrahydrofuran (30 mL) was added to the resulting solution at −100° C. The resulting mixture was heated to −78° C. over one hour, and then stirred at −78° C. for further one hour. A saturated aqueous solution of ammonium chloride was added to terminate the reaction, followed by extraction with ethyl acetate. The resulting organic layer was washed with saturated brine, and then dried over anhydrous magnesium sulfate. After concentration, the resulting crude product was recrystallized from hexane-ethyl acetate to give Compound 3b (2.02 g, 63%).

Synthesis of Compound 3c: Compound 3b (2.02 g, 6.36 mmol) was dissolved in pyridine (12.7 mL), followed by cooling to 0° C. Methanesulfonyl chloride (5.7 mL, 15 mL) was added, and the resulting mixture was stirred at room temperature for two hours. A saturated aqueous solution of sodium bicarbonate was then added to terminate the reaction, and the mixture was extracted with ethyl acetate. The resulting organic layer was washed with saturated brine, dried over anhydrous magnesium sulfate, and then concentrated. Mesylate obtained as the crude product was directly used in the following reaction. The mesylate thus obtained (6.36 mmol) was dissolved in a mixed solvent of dichloromethane (30 mL)-phosphate buffered solution (pH 7, 10 mL), to which 2,3-dichloro-5,6-dicyanobenzoquinone (5.11 g, 22.5 mmol) was added. After stirring at room temperature for three hours, a saturated aqueous solution of sodium bicarbonate was added to terminate the reaction, followed by extraction with ethyl acetate. The resulting mixture was dried over anhydrous magnesium sulfate, and then concentrated. Alcohol obtained as the crude product was directly used in the following reaction. The alcohol thus obtained (6.36 mmol) was dissolved in methanol (32 mL), to which potassium carbonate (4.41 g, 31.9 mmol) was added. After stirring at room temperature for two hours, sodium borohydride (123.3 mg, 3.26 mmol) was added, followed by stirring at room temperature for one hour. Acetone was added to the resulting mixture, followed by filtration. After concentration, saturated brine was added, and the resulting mixture was extracted with ethyl acetate. The resulting organic layer was dried over anhydrous magnesium sulfate, and then concentrated. The resulting residue was purified by silica gel column chromatography (hexane/ethyl acetate=10:1) to give Compound 3c (1.00 g, 88% for 3 steps).

Synthesis of Compound 3d: a solution of lithium diisopropylamide in tetrahydrofuran (10 mL) was prepared from diisopropylamine (1.8 mL, 12.8 mmol) and butyllithium (a 2.6 M hexane solution, 4.2 mL, 10.7 mmol), and cooled to −78° C., to which a mixed solution of Compound 3c (959.9 mg, 5.35 mmol) in tetrahydrofuran (17 mL)-hexamethylphosphoramide (7.5 mL, 42.8 mmol) was added. The resulting mixture was stirred at room temperature for 14 hours, to which chlorotriisopropylsilane (2.9 mL, 13.5 mmol) was added. After stirring at room temperature for 30 minutes, a saturated aqueous solution of sodium bicarbonate was added to terminate the reaction. After extraction with hexane, the resulting organic layer was dried over anhydrous magnesium sulfate. After concentration, the resulting residue was purified by silica gel column chromatography (hexane/ethyl acetate=30:1) to give Compound 3d (915.5 mg, 92%).

Synthesis of Compound 3f: Compound 3d (1.60 g, 4.78 mmol) was dissolved in dichloromethane (24 mL), to which diisobutylaluminum hydride (a 0.97 M hexane solution, 9.9 mL, 9.56 mmol) was added at −78° C. After stirring at 0° C. for two hours, tetrahydrofuran and a 10% aqueous solution of tartaric acid were added to terminate the reaction. After stirring at room temperature for 1.5 hours, the mixture was extracted with hexane. The resulting organic layer was washed with saturated brine, dried over anhydrous magnesium sulfate, and then concentrated. Aldehyde obtained as the crude product was directly used in the following reaction. Sodium hydride (661.7 mg, 27.6 mmol) was added to a solution of diethylphosphonoethyl acetate (3.8 mL, 19.1 mmol) in tetrahydrofuran (10 mL) at 0° C., followed by stirring (hereinbelow, referred to as Solution A). Solution A was added to a solution of the aldehyde thus obtained (4.78 mmol) in tetrahydrofuran at 0° C. After stirring at room temperature for 45 minutes, a saturated aqueous solution of ammonium chloride was added to terminate the reaction. After extraction with hexane, the resulting organic layer was washed with saturated brine, and then dried over anhydrous magnesium sulfate. After concentration, the resulting residue was purified by silica gel column chromatography (hexane/ethyl acetate=50:1) to give Compound 3f (1.39 g, 76% for 2 steps).

Synthesis of Compound 3: diisobutylaluminum hydride (a 0.97 M hexane solution, 10.2 mL, 9.90 mmol) was added to a solution of Compound 3f (1.35 g, 3.30 mmol) in dichloromethane (16.5 mL) at −78° C. The resulting mixture was heated to room temperature over 1.5 hours, followed by stirring at room temperature for 10 minutes. A saturated aqueous solution of potassium sodium tartrate was added to terminate the reaction. After extraction with hexane, the resulting organic layer was washed with saturated brine, and then dried over anhydrous magnesium sulfate. After concentration, the resulting residue was purified by silica gel column chromatography (hexane/ethyl acetate=30:1) to give Compound 3 (1.02 g, 85%).

Compound 3: $^1$H-NMR (500 MHz, CDCl$_3$) δ 5.73 (2H, m), 4.13 (2H, t, J=5.7 Hz), 3.94 (1H, dd, J=10.3, 4.6 Hz), 3.86 (1H, dd, J=10.3, 4.0 Hz), 1.71-1.61 (2H, m), 1.54 (2H, m), 1.28 (2H, m), 1.11-1.01 (21H, m), 0.92 (3H, s), 0.89 (3H, s), 0.66 (3H, s).

Example 7

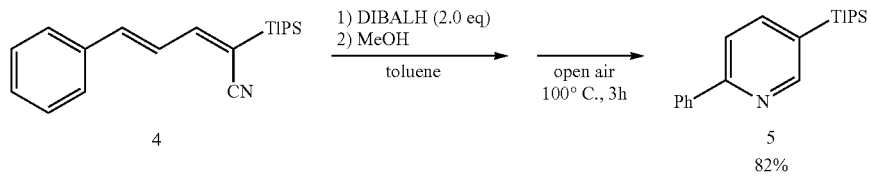

Compound 4 (62 mg, 0.20 mmol) was dissolved in toluene (10 mL), followed by cooling to 0° C. Diisobutylaluminum hydride (a 1.0 M toluene solution, 0.40 mL, 0.40 mmol) was then added, followed by stirring at 0° C. for 15 minutes. Methanol (1.0 mL) was then added to terminate the reaction, followed by stirring at 100° C. for three hours in the air. Slurry silica gel prepared from silica gel (2.5 g)-water (0.8 mL) was added to the resulting reaction solution, and the resulting mixture was stirred at room temperature for 45 minutes. Subsequently, anhydrous magnesium sulfate (33 mg) and potassium carbonate (33 mg) were added, followed by stirring the mixture at room temperature for 90 minutes. The resulting mixture was filtrated through Celite, and then concentrated. The resulting residue was purified by flash column chromatography (silica gel, hexane/ethyl acetate=98.5:1.5) to give Compound 5 (51 mg, 82%).

Compound 5: $^1$H-NMR (500 MHz, CDCl$_3$) δ 8.77 (s, 1H), 8.04 (dt, J=8.0, 1.7 Hz, 2H), 7.85 (dd, J=8.0, 1.7 Hz, 1H), 7.73 (d, J=8.0 Hz, 1H), 7.48 (td, J=8.0, 1.7 Hz, 2H), 7.42 (tt, J=8.0, 1.7 Hz, 1H), 1.45 (sept, J=7.4 Hz, 3H), 1.11 (d, J=7.4 Hz, 18H).

Example 8

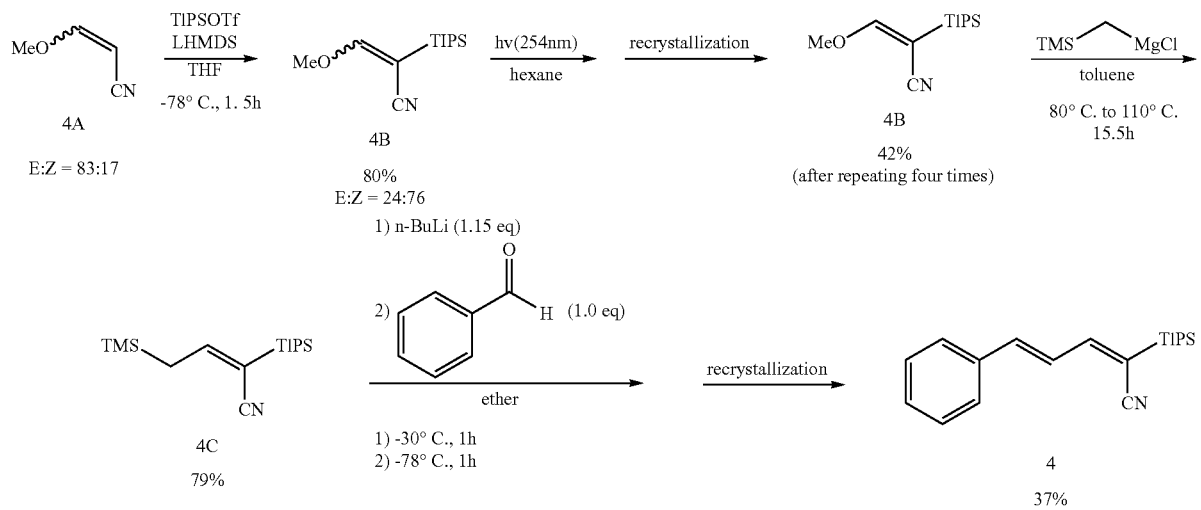

Synthesis of Compound 4B: a solution of lithium hexamethyldisilazide in tetrahydrofuran (125 mL) was prepared from butyllithium (a 2.77 M hexane solution, 78 mL, 217 mmol) and 1,1,1,3,3,3-hexamethyldisilazane (49 mL, 234 mmol), to which 3-methoxyacrylonitrile (E/Z=5:1, 17 mL, 200 mmol) was slowly added at −78° C. Subsequently, a solution of triisopropylsilyl trifluoromethanesulfonate (45 mL, 167 mmol) in tetrahydrofuran (84 mL) was slowly added through a cannula. After stirring at −78° C. for one hour, a saturated aqueous solution of sodium bicarbonate was added to terminate the reaction. After extraction with diethyl ether, the resulting organic layer was washed with saturated brine and then dried over anhydrous magnesium sulfate. After concentration, the resulting crude product was purified by silica gel column chromatography (hexane/ethyl acetate=9/1) to give Compound 4B (32.0 g, 80% based on TIPSOTf) as an inseparable mixture with a ratio of E/Z=24:76. The mixture of the Compound 4B with a ratio of E/Z=24:76 (32.0 g, 134 mmol) thus obtained was dissolved in hexane and then irradiated with a 32 W low pressure mercury lamp at room temperature for four hours in the air. After concentration, the resulting residue was recrystallized from hexane at −30° C. to give Compound 4B as a mono isomer (E-only, 16.6 g, 42%).

Synthesis of Compound 5C: under an argon atmosphere, a solution of chloromethyltrimethylsilane (21 mL, 150 mmol) in diethyl ether (100 mL) was slowly added dropwise to a solution of magnesium flakes (4.38 g, 180 mmol) in diethyl ether (25 mL) while stirring to keep gentle reflux. Toluene (125 mL) was added to the resulting solution, followed by heating to 90° C. to remove diethyl ether. After heating for two hours, the solution was cooled to room temperature (hereinbelow, referred to as Solution A). Under an argon atmosphere, Compound 4B (E-form, 16.3 g, 68 mmol) was dissolved in toluene (272 mL), to which Solution A was added at room temperature, followed by heating to 90° C. After stirring at 90° C. for 15.5 hours, the resulting mixture was cooled to room temperature, to which a saturated aqueous solution of ammonium chloride was added to terminate the reaction. After extraction with hexane, the resulting organic layer was washed with saturated brine, and then dried over anhydrous magnesium sulfate. After concentration, the resulting crude product was purified by silica gel column chromatography (hexane/ethyl acetate=97/3) to give Compound 4C (16.0 g, 74%).

Synthesis of Compound 4: Compound 4C (709.6 mg, 2.4 mmol) was dissolved in diethyl ether (6.0 mL), followed by cooling to −30° C. Butyllithium (a 1.63 M hexane solution, 1.41 mL, 2.3 mmol) was added, followed by stirring at −30° C. for one hour. The resulting mixture was cooled to −78° C., to which a solution of benzaldehyde (0.203 mL, 2.0 mmol) in diethyl ether (4.0 mL) was added. After stirring at −78° C. for one hour, a saturated aqueous solution of ammonium chloride was added to terminate the reaction. After extraction with diethyl ether, the resulting organic layer was dried over anhydrous magnesium sulfate. After concentration, the resulting crude product was recrystallized from hexane at −30° C. to give Compound 4 (233.4 mg, 37%) as a mono isomer.

Compound 4: $^1$H-NMR (500 MHz, CDCl$_3$) δ 7.54-7.53 (m, 2H), 7.41-7.32 (m, 4H), 7.08 (d, J=10.9 Hz, 1H), 6.91 (d, J=15.5 Hz, 1H), 1.34 (sept, J=7.4 Hz, 3H), 1.14 (d, J=7.4 Hz, 18H).

Example 9

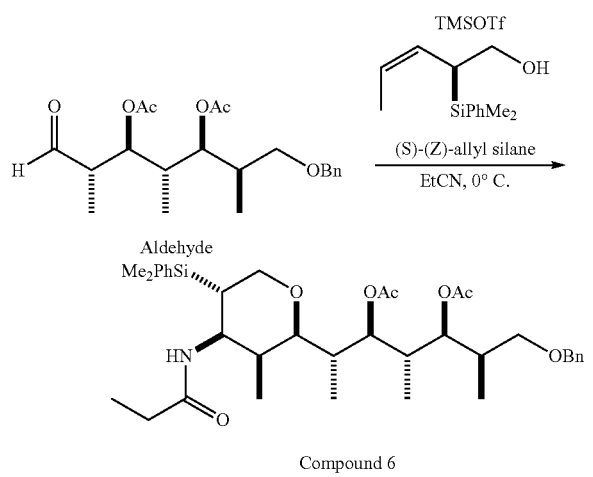

Compound 6

Ac = acetyl, Bn = benzyl, Ph = phenyl
TMS = trimethylsilyl, Et = ethyl

A test tube was charged with aldehyde (0.1 mmol) and (S)—(Z)-allylsilane (33.1 mg, 0.15 mmol) and purged with argon. This mixture was dissolved in dry propionitrile (0.5 mL), followed by stirring at 0° C. Trimethylsilyl trifluoromethanesulfonate (0.36 mg, 0.2 mmol) was slowly added to the resulting solution, followed by stirring at 0° C. for 20 minutes. A saturated aqueous solution of sodium bicarbonate was then added to terminate the reaction, followed by extraction with ethyl acetate. The resulting organic layer was dried over anhydrous magnesium sulfate, and the solvent was removed. The resulting crude product was purified by flash column chromatography (silica gel) to give Compound 6 with the yield of 66%.

Compound 6: $^1$H-NMR (500 MHz, CDCl$_3$) δ 7.54-7.21 (10H, m), 5.02 (1H, dd, J=6.3, 4.0 Hz), 4.95 (1H, dd, J=6.9, 4.0 Hz), 4.78 (1H, d, J=8.6 Hz), 4.47 (1H, d, J=12.0 Hz), 4.42 (1H, d, J=12.0 Hz), 4.10 (1H, ddd, J=12.6, 8.6, 4.0 Hz), 3.93 (1H, dd, J=11.5, 4.6 Hz), 3.37-3.18 (4H, m), 2.45 (1H, d, J=6.9 Hz), 2.19-2.07 (1H, m), 2.07-1.89 (2H, m), 2.02 (3H, s), 1.99 (3H, s), 1.72 (1H, dq, J=14.9, 7.4 Hz), 1.66 (1H, dq, J=14.9, 7.4 Hz), 1.47 (1H, ddd, J=12.6, 12.6, 4.6 Hz), 0.96 (3H, d, J=6.9 Hz), 0.94 (6H, d, J=6.9 Hz), 0.87 (3H, d, J=6.9 Hz), 0.78 (3H, d, J=7.4 Hz), 0.73 (3H, d, J=6.9 Hz), 0.34 (3H, s), 0.21 (3H, s).

Example 10

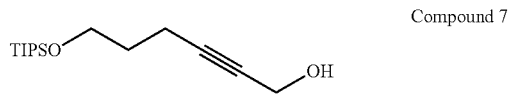

Compound 7: in a similar manner to the method for synthesizing Compound 8 from Compound 8A as will be described in the following Example 11, 5-(triisopropylsilyl)-1-pentyne was obtained from commercially available 1-pentyne-5-ol, which was then converted to Compound 7 in accordance with the method described in the literature (J. R. Granja et al., Journal of Organic Chemistry, 2005, 70, 8281 to 8290).

Colorless oily product: $^1$H-NMR (500 MHz, CDCl$_3$) δ 1.00-1.15 (21H, m), 1.68-1.81 (2H, m), 2.28-2.40 (2H, m), 3.73-3.78 (2H, m), 4.24 (2H, dt, J=5.2, 2.3 Hz).

Example 11

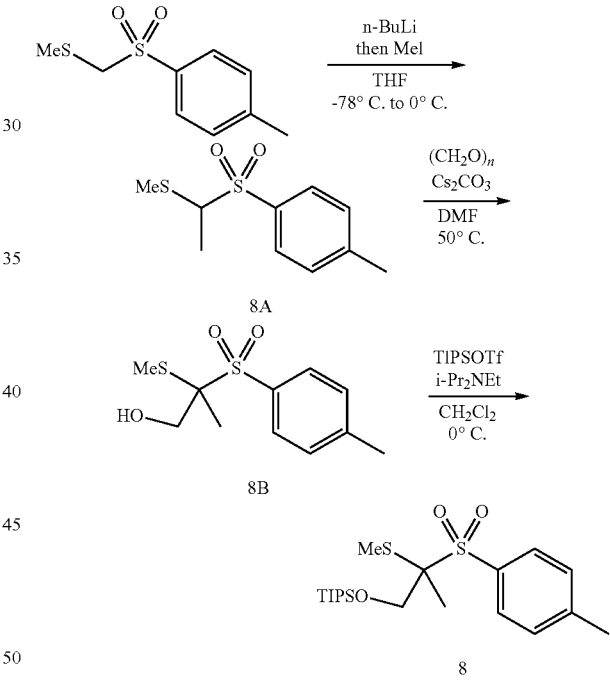

Synthesis of Compound 8A: Commercially available methylthiomethyl p-tolyl sulfone (11.3 g, 52.1 mmol) was dissolved in tetrahydrofuran (350 mL), to which butyllithium (a 2.64 M hexane solution, 21 mL, 55.4 mmol) was added at −78° C. After stirring for 1.5 hours, methyl iodide (6.5 mL, 104 mmol) was added. After stirring at 0° C. for 30 minutes, an aqueous solution of ammonium chloride was added to terminate the reaction, followed by extraction with ethyl acetate. The resulting organic layer was washed with saturated brine, and then water, and dried over magnesium sulfate. The solvent was removed under reduced pressure. The resulting product was recrystallized from hexane-ethanol to give Compound 8A with the yield of 56%. The Compound 8A thus obtained contained approximately 5% of the raw material and approximately 5% of the compound in the dimethylated form.

Synthesis of Compound 8B: Compound 8A (1.93 g, 8.37 mmol) was dissolved in N,N-dimethylformamide (8.4 mL), to which paraformaldehyde (756 mg, 25.2 mmol) and cesium carbonate (140 mg, 0.43 mmol) were added, followed by heating at 50° C. for 30 minutes. An aqueous solution of ammonium chloride was added to terminate the reaction, followed by extraction with ethyl acetate. The resulting organic layer was dried over magnesium sulfate, and the solvent was removed under reduced pressure. The resulting product was purified by silica gel column chromatography (ethyl acetate/hexane=30% to 50%) to give Compound 8B with the yield of 80%.

Synthesis of Compound 8: triethylamine (3.5 mL, 20 mmol) was added to a solution of Compound 8B (1.75 g, 6.71 mmol) in dichloromethane (34 mL), followed by cooling to 0° C. Triisopropylsilyl trifluoromethanesulfonate (2.7 mL, 10 mmol) was added dropwise over one minute, followed by stirring at 0° C. for three hours. A saturated aqueous solution of sodium bicarbonate was then added to terminate the reaction, followed by extraction with ethyl acetate. The resulting organic layer was dried over magnesium sulfate, and the solvent was removed under reduced pressure. The resulting product was purified by silica gel column chromatography (ethyl acetate/hexane=2% to 10%) to give Compound 8 as a mixture of Compound 8 and TIPSOH with a molar ratio of approximately 55:45.

Compound 8: $^1$H-NMR (500 MHz, CDCl$_3$) δ 7.83 (d, J=8.6 Hz, 3H), 7.32 (d, J=8.6 Hz, 3H), 4.10 (s, 3H), 2.45 (s, 3H), 2.28 (s, 3H), 1.56 (s, 3H), 1.07-1.00 (m, 21H).

Reference Example 1

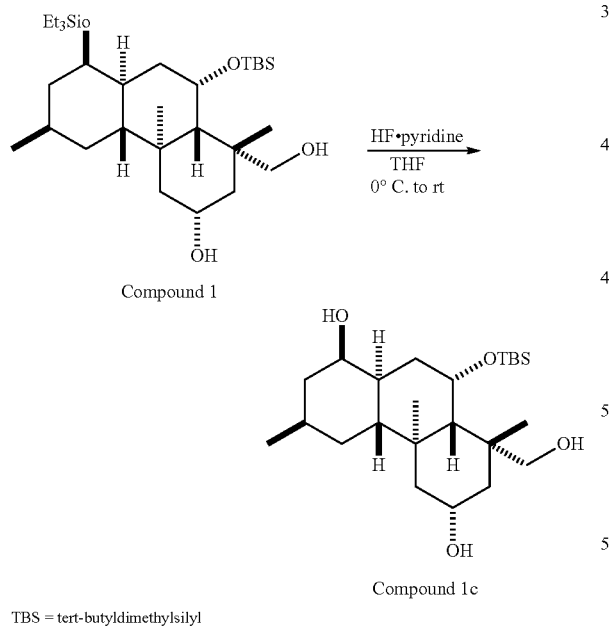

Compound 1c

TBS = tert-butyldimethylsilyl
Et = ethyl, THF = tetrahydrofuran

A polypropylene 5 mL test tube was charged with Compound 1 (5.5 mg, 10.2 mmol) and purged with argon, and Compound 1 was dissolved in dry tetrahydrofuran (0.3 mL), followed by cooling to 0° C. After addition of hydrogen fluoride-pyridine (0.15 mL) using a polypropylene syringe, the resulting mixture was stirred at room temperature for 1.5 hours. At 0° C., methoxytrimethylsilane (approximately 1.5 mL) was slowly added over one hour until the pH of the resulting reaction solution reached 7. The resulting reaction solution was concentrated, and then dried under greatly reduced pressure. The resulting residue was purified by flash column chromatography (silica gel, chloroform/methanol=9/1) to give Compound 1c as a colorless crystal (3.2 mg, >99%).

Compound 1c: $^1$H-NMR (500 MHz, CD$_3$OD) δ 1.10 (3H, s), 1.18 (3H, d, J=7.5 Hz), 1.37 (3H, s), 1.31-1.48 (5H, m), 1.55-1.82 (7H, m), 1.88-1.95 (1H, m), 2.00-2.09 (1H, m), 3.22 (1H, d, J=12.1 Hz), 3.79 (brd, J=2.3 Hz), 4.08 (1H, quintet, J=4.0 Hz), 4.41 (1H, s), 4.64 (1H, d, J=12.0 Hz).

Comparative Example 2

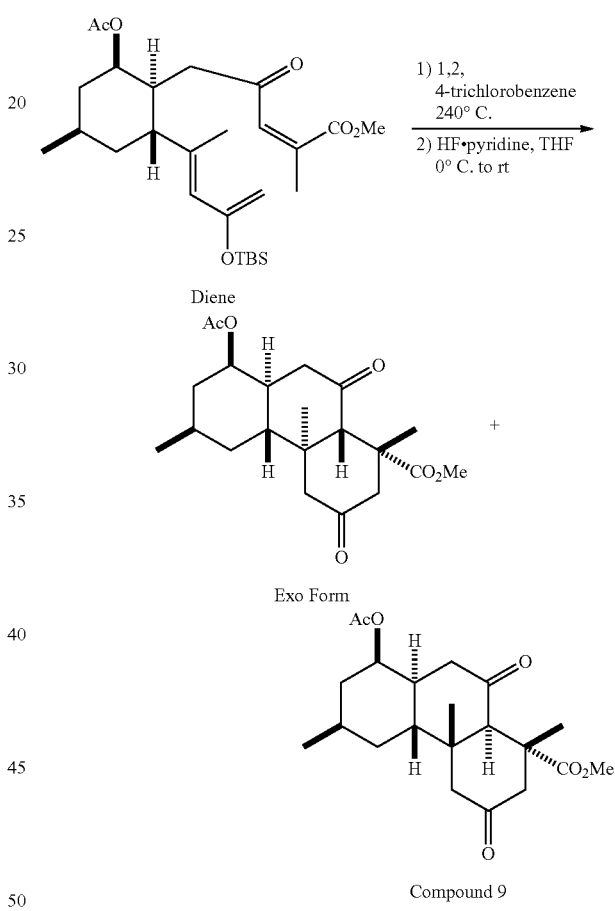

TBS = tert-butyldimethylsilyl
Ac = acetyl, Me = methyl

A flask was purged with argon and then charged with dry 1,2,4-trichlorobenzene (22 mL), followed by heating to 240° C., to which a solution of diene (10.7 g, 21.8 mmol) (Miyashita, M. et al., Science 2004, 305, 495) in 1,2,4-trichlorobenzene (22 mL) was slowly added dropwise over one hour. After stirring at 240° C. for 0.5 hour, the resulting mixture was cooled to room temperature. The resulting reaction solution was directly purified by silica gel column chromatography (hexane/ethyl acetate=9/1 to 3/1) to give a cyclic compound.

A flask was charged with the cyclic compound thus obtained (21.8 mmol), and then purged with argon. The cyclic compound was dissolved in dry tetrahydrofuran (33 mL). After cooling to 0° C., 70% hydrogen fluoride-pyridine (4.4 mL) was added. The resulting mixture was stirred at room temperature for three hours, to which a saturated aqueous solution of sodium bicarbonate was added to terminate the reaction. After extraction with ethyl acetate, the resulting organic layer was washed with water and saturated brine. The resulting product was dried over anhydrous magnesium sulfate, and the solvent was removed. The resulting crude product was recrystallized from hexane-ethyl acetate to give a compound in the exo form (4.4 g, 51% for 2 steps) as a colorless crystal. The mother liquid was concentrated and then recrystallized from hexane-ethyl acetate to give Compound 9 as a colorless crystal.

Compound 9: $^1$H-NMR (270 MHz, CDCl$_3$) δ 1.13 (d, J=7.4 Hz, 3H), 1.20 (dd, J=12.7, 4.6 Hz, 1H), 1.28 (s, 3H), 1.38 (s, 3H), 1.61-2.25 (m, 8H), 2.11 (s, 3H), 2.23 (d, J=3.8, 11.7 Hz, 1H), 2.50 (d, J=14.7 Hz, 1H), 2.59 (bt, J=12.6 Hz, 1H), 3.18 (s, 1H), 3.24 (d, J=14.7 Hz, 1H), 3.65 (s, 3H), 4.94-4.95 (m, 1H).

Comparative Example 3

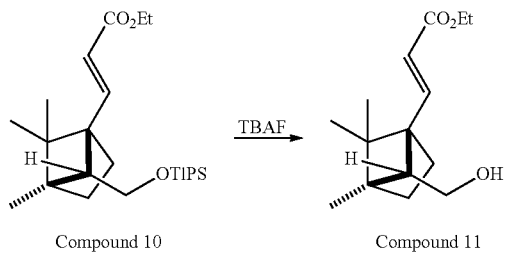

Compound 10 → Compound 11

At room temperature, tetrabutylammonium fluoride (a 1.0 M tetrahydrofuran solution, 14 mL, 14.0 mmol) was added to Compound 10 (3.9 g, 9.5 mmol). After stirring at room temperature for one hour, water was added to terminate the reaction. After extraction with ethyl acetate, the resulting organic layer was dried over anhydrous magnesium sulfate, and the solvent was removed. The resulting crude product was purified by silica gel column chromatography (hexane/ethyl acetate=18:1) to give Compound 11 (2.15 g, 90%).

Compound 11: $^1$H-NMR (500 MHz, CDCl$_3$) δ 6.97 (1H, d, J=16.0 Hz), 5.82 (1H, d, J=16.0 Hz), 4.17 (2H, q, J=7.4 Hz), 3.50 (2H, d, J=6.3 Hz), 2.27 (1H, t, J=6.3 Hz), 1.72 (2H, m), 1.60-1.50 (2H, m), 1.46 (1H, m), 1.29 (3H, t, J=7.4 Hz), 1.06 (3H, s), 0.97 (3H, s), 0.74 (3H, s).

Comparative Example 4

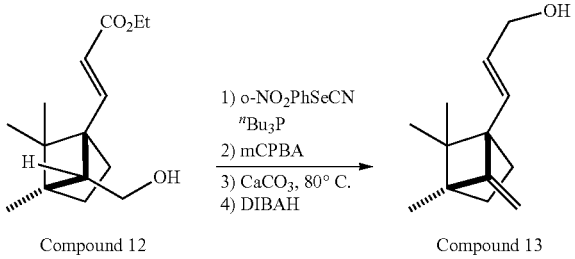

Compound 12 → Compound 13

1) o-NO$_2$PhSeCN
$^n$Bu$_3$P
2) mCPBA
3) CaCO$_3$, 80° C.
4) DIBAH

Butylphosphine (0.75 mL, 3.0 mmol) was added to a solution of Compound 12 (506.4 mg, 2.0 mmol) and 2-nitrophenyl selenocyanate (727.2 mg, 3.2 mmol) in tetrahydrofuran (10 mL) at 0° C. After stirring at room temperature for two hours, the resulting mixture was concentrated, and then filtrated by silica gel column chromatography (hexane/ethyl acetate=18:1). Selenide obtained as the crude product was directly used in the following reaction. To a solution of the selenide thus obtained (2.0 mmol) in dichloromethane (10 mL), m-chloroperbenzoic acid (75%, 599.7 mg, 2.6 mmol) was added, followed by stirring at room temperature for 15 minutes. After addition of 2-methyl-2-butene (0.22 mL, 2.0 mmol), the resulting mixture was stirred at room temperature for 10 minutes, to which a saturated aqueous solution of sodium bicarbonate and diethyl ether were added. After concentration, the resulting mixture was extracted with ethyl acetate. The resulting organic layer was dried over anhydrous magnesium sulfate, and then concentrated. Selenoxide obtained as the crude product was directly used in the following reaction. Calcium carbonate (1.25 g, 12.5 mmol) was added to a solution of the selenoxide thus obtained (2.0 mmol) in toluene (13 mL), followed by stirring at 80° C. for one hour. After addition of hexane, the resulting mixture was filtrated through Celite. After concentration, the resulting residue was purified by silica gel column chromatography (hexane/ethyl acetate=30:1) to give olefin (273.2 mg, 58% for 3 steps). The olefin thus obtained (484.6 mg, 2.07 mmol) was dissolved in tetrahydrofuran (7 mL), to which diisobutylaluminum hydride (6 mL, 6.2 mmol) was added at −78° C. After stirring at −78° C. for 30 minutes, a saturated aqueous solution of tartaric acid was added to terminate the reaction. After extraction with ethyl acetate, the resulting organic layer was dried over anhydrous magnesium sulfate, and then concentrated. The resulting residue was purified by silica gel column chromatography (hexane/ethyl acetate=15:1) to give Compound 13 (353.6 mg, 89%).

Compound 12: $^1$H-NMR (500 MHz, CDCl$_3$) δ 5.74 (2H, m), 4.36 (2H, d, J=7.4 Hz), 4.16 (2H, m), 1.77 (1H, m), 1.63 (2H, m), 1.55 (1H, m), 1.29 (1H, brs), 0.97 (3H, s), 0.95 (3H, s), 0.76 (3H, s).

Test Example 1

The PPM1D-inhibitory activity of the compound of the present invention (1) was measured.

Method

Into a pColdI vector (TaKaRa Bio Inc.), cDNA encoding the catalytic domain (the positions 1 to 420) of PPM1D protein (Protein ID: O15297/cDNA ID: U70385) was introduced, and the PPM1D protein was expressed in *E. coli* as a His tag fusion protein. The protein of interest was purified by metal affinity chromatography with BD-TALON resin (CLONTECH), and then eluted with an elution buffer (150 mM imidazole, PBS (pH 7.5), 500 mM NaCl, 10% glycerol, 0.2% ethanol, and 1 mM 2-mercaptoethanol). The PPM1D protein thus eluted was dialyzed against a dialysis buffer (50 mM Tris-HCl (pH 7.5), 0.1 mM EGTA, and 0.02% 2-mercaptoethanol) for 16 hours, and then stored at −80° C. as a 50% glycerol stock (an enzyme concentration of 1 µM).

The enzyme that was expressed and purified by the aforementioned method was used for analysis of the inhibitory effect of the compound on PPM1D. Also, as a substrate, a phospho-p53 (Ser 15)-containing peptide (Ac-Val-Glu-Pro-Pro-Leu-Ser(P)-Gln-Glu-Thr-Phe-Ser-Asp-Leu-Trp-NH$_2$: Ser(P) indicates phosphorylated Ser) chemically-synthesized by the Fmoc solid phase method was used. A purified phospho-p53 peptide was dissolved in H$_2$O to prepare a 400 µM original substrate solution. The test compound of Example 1 (inhibitor) was dissolved in ethanol (EtOH) to a concentration of 40 mM, and then diluted with dimethyl sulfoxide (DMSO)

to adjust an original inhibitor solution with a concentration of 4 mM in advance. Other inhibitors were dissolved in dimethyl sulfoxide (DMSO) to prepare original inhibitor solutions with a concentration of 4 mM. 30 μL of a mixed solution of the inhibitor and the substrate (66.7 μM phosphorylated peptide substrate, 66.7 μM inhibitor, 1.7% DMSO (in the case of Example 1, 1.5% DMSO and 0.2% EtOH), and 13 mM Tris-HCl (pH 8.0)) was kept warm at 30° C., to which 20 μL of a mixed solution of an enzyme and a metal ion kept at 4° C. (10 nM PPM1D, 125 mM Tris-HCl (pH 7.5), 0.25 mM EGTA, 0.05% 2-mercaptoethanol, and 75 mM $MgCl_2$) was added. The resulting mixture was incubated at 30° C. for 10 minutes, and then the inhibitory activity on PPM1D was measured. The enzyme reaction was terminated with addition of 100 μL of a BIOMOL GREEN reagent (Biomol), and 30 minutes later, the absorbance at 620 nm was measured to detect phosphoric acid freed by PPM1D. The inhibitory effect on PPM1D was analyzed by measuring, from the absorbance measured at 620 nm, the amount of free phosphoric acid reduced due to the addition of the inhibitor with respect to the amount of free phosphoric acid in the case of addition of DMSO not including the inhibitor.

Result

The results thus obtained are shown in Table 1.

TABLE 1

| Test compound | Rate of PPM1D inhibition (4 μM: %) |
|---|---|
| Example 1 | 97.1 ± 2.49 |
| Example 2 | 87.1 |
| Example 3 | 79.4 |
| Example 4 | 25.1 |
| Example 5 | 92.7 ± 1.40 |
| Example 6 | 41.0 ± 2.90 |
| Example 7 | 70.7 ± 2.74 |
| Example 8 | 69.7 ± 3.42 |
| Example 9 | 43.6 ± 2.89 |
| Example 10 | 35.4 ± 2.18 |
| Example 11 | 33.7 ± 4.78 |
| Comparative Example 1 | 0 |
| Comparative Example 2 | 0 |
| Comparative Example 3 | 0 |
| Comparative Example 4 | 0 |

Test Example 2

The PPM1D-inhibitory activity was measured to examine the selectivity of the PPM1D-inhibitory activity of the compound of the present invention (1). The results of the compound of Example 1 [Compound 1] and the compound of Example 5 [Compound 2] are shown in Table 2.

Method

In order to analyze the enzyme selectivity of the inhibitor, the inhibitory effect on PPM1A, which belongs to the PPM1 family as PPM1D does, was analyzed and compared with the inhibitory effect on PPM1D. Into a pColdI vector, cDNA encoding full length PPM1A (382 residues) (Protein ID: P35813/cDNA ID: S87759) was introduced, and the PPM1A was expressed in *E. coli* and then purified similarly to PPM1D. The inhibitory activity on 16 nM purified PPM1A was measured. As a substrate of PPM1A, a phospho-p38 peptide analog (Ac-Asp-Asp-Glu-Nle-Thr(P)-Gly-Tyr(P)-Val-Ala-Thr-Arg-$NH_2$: Thr(P), Tyr(P), and Nle indicate phosphorylated Thr, phosphorylated Tyr, and norleucine, respectively) was used.

30 μL of a mixed solution of the inhibitor and the substrate (66.7 μM phosphorylated peptide substrate, each concentration of the inhibitor, 1.7% DMSO (for the test compound of Example 1, 1.5% DMSO and 0.2% EtOH), and 13 mM Tris-HCl (pH 8.0)) was kept warm at 30° C., to which 20 μL of a mixed solution of an enzyme and a metal ion kept at 4° C. (40 nM PPM1A, 125 mM Tris-HCl (pH 7.5), 0.25 mM EGTA, 0.05% 2-mercaptoethanol, and 25 mM $MnCl_2$) was added. The resulting mixture was incubated at 30° C. for 10 minutes, and then the inhibitory activity on PPM1A was measured.

Also, in order to analyze the enzyme selectivity of the inhibitor within the Ser/Thr phosphatase family, the inhibitory effect on PP2A (Protein ID: P67775/cDNA ID: X12649), which belongs to the PPP family, was analyzed. PP2A was purchased from Promega K.K. As a substrate of PP2A, a phospho-p38 peptide analog (Ac-Thr-Asp-Asp-Glu-Met-Thr(P)-Gly-Tyr-Val-Ala-Thr-$NH_2$: Thr(P) indicates phosphorylated Thr) was used. 30 μL of a mixed solution of the inhibitor and the substrate (333.3 μM phosphorylated peptide substrate, each concentration of the inhibitor, 1.7% DMSO (in the case of Example 1, 1.5% DMSO and 0.2% EtOH), and 13 mM Tris-HCl (pH 8.0)) was kept warm at 30° C., to which 20 μL of a mixed solution of an enzyme and a metal ion kept at 4° C. (25 mU PP2A, 125 mM Tris-HCl (pH 7.5), 0.25 mM EGTA, 0.05% 2-mercaptoethanol, and 75 mM $MgCl_2$) was added. The resulting mixture was incubated at 30° C. for 10 minutes, and then the inhibitory activity on PP2A was measured.

The inhibitory activity on PPM1A, PP2A, and PPM1D at each final concentration of the inhibitor (0, 0.1, 0.2, 0.4, 1, 2, 4, 10, or 40 μM) was measured three times with respect to each concentration, and the concentration of the inhibitor required for 50% inhibition of the enzyme activity ($IC_{50}$) was determined.

The original inhibitor solution was diluted with a solvent (DMSO, (for the test compound of Example 1, 90% DMSO and 10% EtOH)) to prepare each concentration of an inhibitor solution.

Other conditions for measurement of the enzyme activity are the same as those in Test Example 1.

The enzyme selectivity of the inhibitor was analyzed by comparing the $IC_{50}$ values of the inhibitor on PPM1D, PPM1A, and PP2A.

Also, the inhibition constant of the inhibitor (Ki) and the inhibition pattern were measured as follows.

The enzyme that was expressed and purified by the method demonstrated in Test Example 1 was used for analysis of the inhibition constant and the inhibition pattern of the compound on PPM1D. As a substrate, a phospho-p53 (Ser 15) peptide analog (Ac-Val-Glu-Pro-Pro-Leu-Ser(P)-Gln-Glu-Thr-Phe-Ser-Asp-Leu-Trp-$NH_2$: Ser(P) indicates phosphorylated Ser) was used. 30 μL of a mixed solution of the inhibitor and the substrate (each concentration of the phosphorylated peptide substrate, each concentration of the inhibitor, 1.7% DMSO (in the case of Example 1, 1.5% DMSO and 0.2% EtOH), and 13 mM Tris-HCl (pH 8.0)) was kept warm at 30° C., to which 20 μL of a mixed solution of an enzyme and a metal ion kept at 4° C. (10 nM PPM1D, 125 mM Tris-HCl (pH 7.5), 0.25 mM EGTA, 0.05% 2-mercaptoethanol, and 75 mM $MgCl_2$) was added. The resulting mixture was incubated at 30° C. for 10 minutes, and then the inhibitory activity on PPM1D was measured.

The activity on PPM1D was measured at each concentration of the phosphorylated peptide substrate (5, 10, 20, and 40

μM), and at each final concentration of the inhibitor (0, 0.3, 0.4, and 0.6 μM (the compound of Example 1 [Compound 1]) or 0, 0.4, and 1.2 μM (the compound of Example 5 [Compound 2]). The enzyme reaction was terminated with addition of 50 μL of a BIOMOL GREEN reagent (Biomol) to a reaction solution, and 30 minutes later, the absorbance at 620 nm was measured to detect phosphoric acid freed by PPM1D.

Based on the results thus obtained, Ki (μM) was calculated.
Result

The selectivity of the compound of the present invention for PPM1D was evaluated using the compound of Example 1 [Compound 1]. As a result, the $IC_{50}$ value for PPM1D was found to be: 0.43±0.04 μM, and that for PPM1A was found to be: 21±1.7 μM.

Further, the results obtained using the compound of Example 1 [Compound 1] and the compound of Example 5 [Compound 2] are shown in Table 2.

As described above, the inhibitory activity of the compound of the present invention was extremely selective for PPM1D.

TABLE 2

Evaluation on selectivity of PPM1D inhibitor

| Compound | Ki (μM) | PPM1D $IC_{50}$ (μM) | PPM1A $IC_{50}$ (μM) | PP2A $IC_{50}$ (μM) |
|---|---|---|---|---|
| Compound 1 | 0.59 ± 0.05 | 0.48 ± 0.04 | 21 ± 1.7 | [a]N.A. |
| Compound 2 | 2.6 ± 0.1 | 0.93 ± 0.04 | 28 ± 4.2 | [b]N.A. |

N.A. not available
[a]11% inhibition of the PP2A activity with addition of 40 μM inhibitor.
[b]14% inhibition of the PP2A activity with addition of 40 μM inhibitor.

Test Example 3

A cancer suppressor protein p53 is activated and stabilized upon DNA damage, and induces expression of a number of proteins involved in cell-cycle arrest and apoptosis to prevent canceration of a cell. The p53 is activated upon phosphorylation, and particularly phosphorylation of Ser at the position 15 is reported to play an important role in activation and stabilization of p53.

PPM1D is known to dephosphorylate phosphorylated Ser at the position 15 of p53. From among the PPM1D inhibitors obtained by screening, the compound of Example 1 [Compound 1] or the compound of Example 5 [Compound 2] was added to MCF7 cells (breast cancer-derived cells, overly expressing PPM1D) to measure the effect of the inhibitor in the cells.
Method 1

MCF7 cells were stimulated with adriamycin (ADR: alternative name, doxorubicin), to which the compound of Example 1 [Compound 1] (10 μM) was added. The PPM1D-inhibitory activity of Compound 1 in the cells was measured by observing phosphorylation of Ser at the position 15 of p53 after 12 hours. As a control, similar operations were performed on MCF7 cells without stimulation of ADR (−).

Subsequently, p53 was concentrated by isoelectric precipitation using FL393, an anti-p53 polyclonal antibody, and phospho-p53 (Ser 15) was detected by Western blotting.
Method 2

Figure 2:
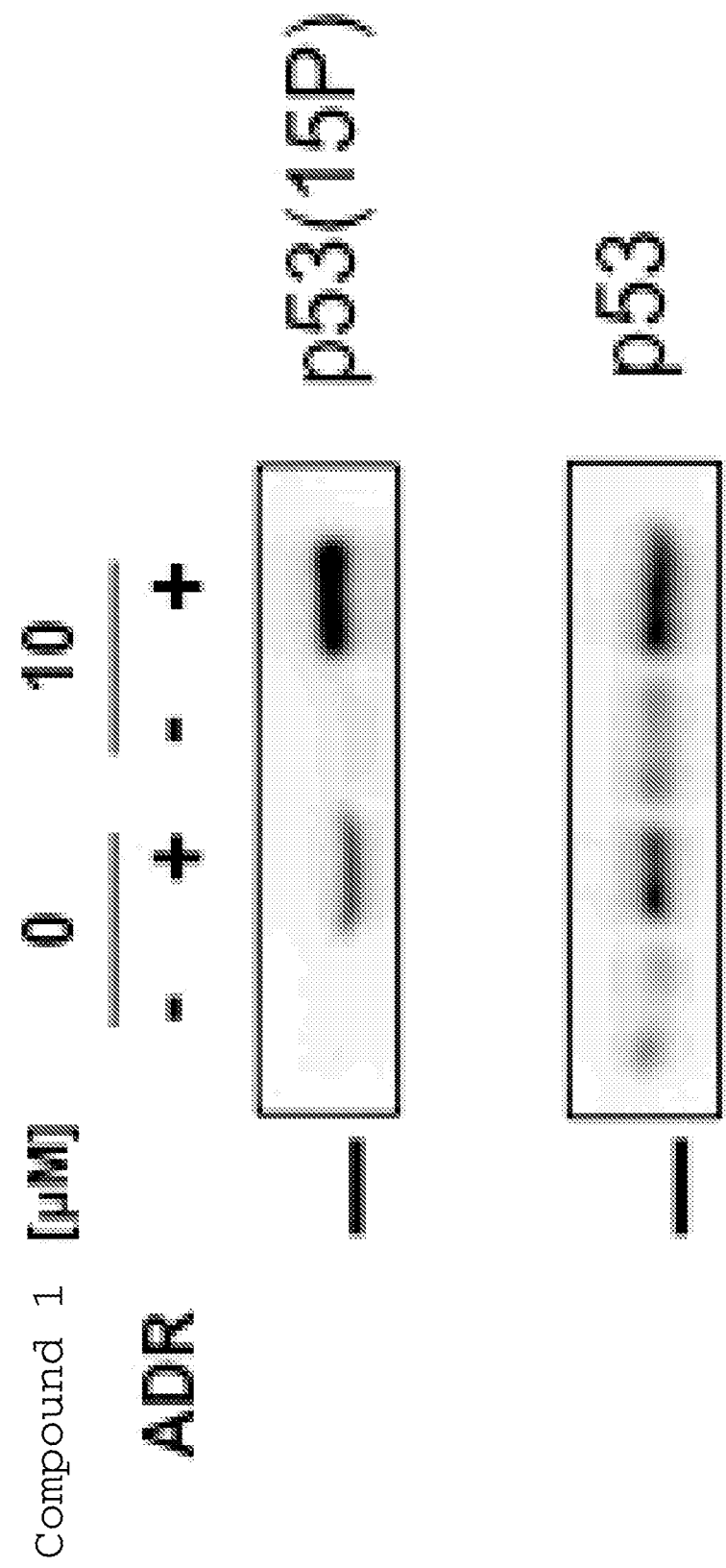
FIG. 2 is a diagram showing the effect of the compound of Example 1 (Compound (1)) on adriamycin (ADR)-stimulated (+) breast cancer-derived MCF7 cells. The symbol (−) indicates the cells without stimulation of ADR (upper diagram: phospho-p53 (Ser 15), lower diagram: the total amount of p53 protein, * bar indicates the 47.5 kDa marker)
Figure 3:
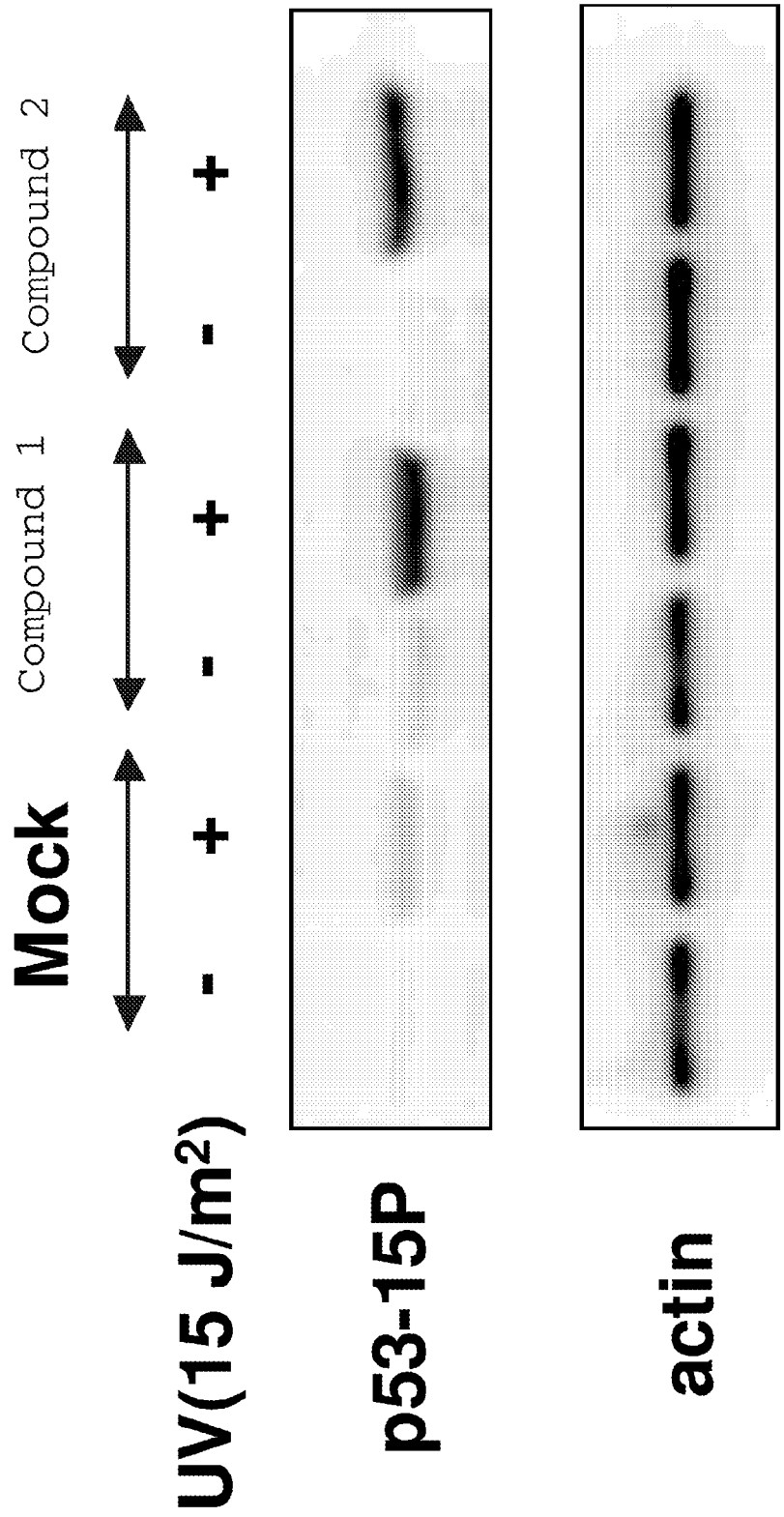
FIG. 3 is a diagram showing the effects of the compound of Example 1 (Compound (1)) and the compound of Example 5 (Compound (2)) on UV (15 J/m$^2$)-stimulated (+) breast cancer-derived MCF7 cells. The symbol (−) indicates the cells without stimulation of UV (upper diagram: phospho-p53 (Ser 15), lower diagram: comparison of the amount of protein with actin)

MCF7 cells were irradiated with UV (15 J/m²), to which the compound of Example 1 [Compound 1] or the compound of Example 5 [Compound 2] (10 μM) was added. The PPM1D-inhibitory activity of the compound of Example 1 [Compound 1] or the compound of Example 5 [Compound 2] in the cells was measured by observing phosphorylation of Ser at the position 15 of p53 after 24 hours. Changes in the amount of phospho-p53 (Ser 15) were detected by Western blotting. As the primary antibody, a mouse anti-phospho-p53 (Ser15) monoclonal antibody 16-G8 (Cell Signaling Technology, Inc.) was used, and as the secondary antibody, an anti-mouse IgG-HRP antibody (GE Healthcare Bioscience) was used. As a control, similar operations were performed on MCF7 cells without irradiation of UV (−). Phospho-p53 (Ser 15) was detected similarly to the aforementioned Method 1.
Result Addition of the compound of the present invention (1) greatly increased phosphorylated p53, indicating activation of p53 (FIGS. 2 and 3).

Test Example 4

The effect of the compound of the present invention (1) on cancer cells was verified.
Method In a DMEM medium (10% FBS, 2 mM glutamine, and 100 nM penicillin/streptomycin) in a 10 cm dish, 1.1×10⁵ breast cancer-derived MCF7 cells (purchased from ATCC) were cultured for 18 hours under conditions of 5% $CO_2$ at 37° C. And then, the PPM1D inhibitor (Compound 1: 40 μM, 0.06% DMSO, 0.12% EtOH/Mock: 0.06% DMSO and 0.12% EtOH) was added, and 72 hours after addition of the inhibitor, transmission images of the cells were observed with BIOREVO BZ-8000 (Keyence Corporation). Subsequently, the cells were washed with 5 ml PBS (8.1 mM $Na_2HPO_4$, 2.68 mM KCl, 1.47 mM $KH_2PO_4$, 137 mM NaCl, pH7.5) twice, and then collected using a 0.25% trypsin/EDTA solution (GIBCO), to which trypan blue was added. The cell count was then measured using a hemocytometer.
Result The compound of the present invention (1) was shown to have an inhibitory action on cancer cell proliferation (FIGS. 4 and 5).

The invention claimed is:
1. A silicon compound represented by the formula (2) or a salt thereof:

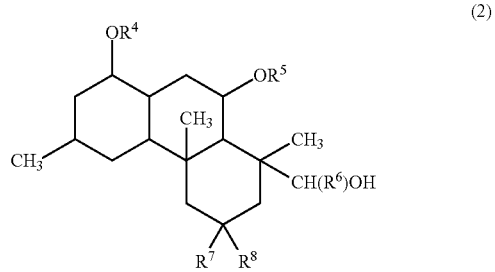

(2)

wherein $R^4$ and $R^5$ are the same or different and represent a hydrogen atom or $(R^1)(R^2)(R^3)Si$—, wherein at least one of $R^4$ and $R^5$ is $(R^1)(R^2)(R^3)Si$—;
$R^1$, $R^2$, and $R^3$ are the same or different and represent a hydrocarbon group having 1 to 12 carbon atoms;

$R^6$ represents a hydrogen atom or optionally forms —O— (ether bond) together with the hydroxyl group of $R^8$; and $R^7$ represents a hydrogen atom and $R^8$ represents a hydroxyl group, or $R^7$ and $R^8$ optionally together form an oxo group (=O).

2. The silicon compound or the salt thereof according to claim 1, wherein the silicon compound is represented by the following formula (2-1), (2-2), or (2-3):

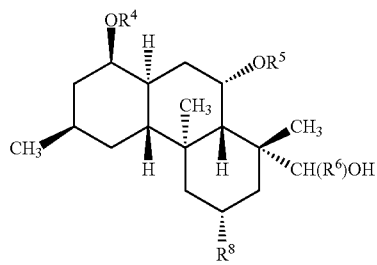
(2-1)

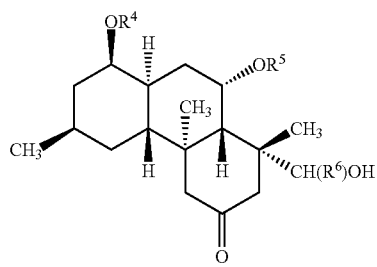
(2-2)

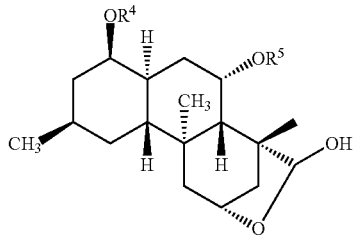
(2-3)

wherein $R^4$, $R^5$, $R^6$ and $R^8$ are as defined above, or a salt thereof.

3. The silicon compound or the salt thereof according to claim 1, wherein $R^1$, $R^2$, and $R^3$ are the same or different and represent linear or branched alkyl group having 1 to 8 carbon atoms, an aromatic hydrocarbon group having 6 to 14 carbon atoms, or a $C_{6-10}$ aryl-$C_{1-6}$ alkyl group.

4. The silicon compound or the salt thereof according to claim 1, wherein $(R^1)(R^2)(R^3)Si$— is selected from the group consisting of a trimethylsilyl group, a triethylsilyl group, a tri(n-propyl)silyl group, a triisopropylsilyl group, a tri(n-butyl)silyl group, a tri(sec-butyl)silyl group, a triisobutylsilyl group, a tert-butyldimethylsilyl group, a dimethylphenylsilyl group, a methyldiphenylsilyl group, a triphenylsilyl group, and a tert-butyldiphenylsilyl group.

5. A composition comprising the silicon compound or the salt thereof according to claim 1, and a pharmaceutically acceptable carrier.

6. A protein phosphatase inhibitor comprising the silicon compound or the salt thereof according to claim 1.

7. The protein phosphatase inhibitor according to claim 6, wherein the protein phosphatase inhibitor is a PPM1D inhibitor.

\* \* \* \* \*